(12) United States Patent
Laster et al.

(10) Patent No.: US 6,450,812 B1
(45) Date of Patent: Sep. 17, 2002

(54) BI-CORTICAL DENTAL IMPLANT

(75) Inventors: Zvi Laster, Por's Ilit; Simon Girshovich, Kfar-Saba; Daniel Baruc, Naharia, all of (IL)

(73) Assignee: Advanced Dental Engineering Ltd, Katzria (IL)

( * ) Notice: Subject to any disclaimer, the term of this patent is extended or adjusted under 35 U.S.C. 154(b) by 0 days.

(21) Appl. No.: 09/925,390

(22) Filed: Aug. 9, 2001

(30) Foreign Application Priority Data

Sep. 9, 2000 (IL) .................................. 138457

(51) Int. Cl.⁷ .............................. A61C 8/00; A61C 3/00
(52) U.S. Cl. ......................... 433/173; 433/75; 433/174
(58) Field of Search ..................... 433/75, 173, 174, 433/175, 176

(56) References Cited

U.S. PATENT DOCUMENTS

| | | |
|---|---|---|
| 3,436,826 A | 4/1969 | Edelman |
| 3,981,079 A * | 9/1976 | Lenczycki ................. 433/174 |
| 4,044,466 A * | 8/1977 | Pasqualini et al. .......... 433/176 |
| 4,084,318 A | 4/1978 | McEachern |
| 4,789,801 A | 12/1988 | Lee |
| 4,828,492 A * | 5/1989 | Agnone ..................... 433/173 |
| 5,542,847 A * | 8/1996 | Margulies .................. 433/173 |
| 5,611,688 A | 3/1997 | Hanosh |
| 5,702,346 A | 12/1997 | Lazzara |
| 5,797,741 A * | 8/1998 | Bonpard et al. ............ 433/173 |
| 5,951,288 A | 9/1999 | Sawa |
| 6,015,294 A | 1/2000 | Lauks |
| 6,135,773 A * | 10/2000 | Lazzara ..................... 433/173 |

FOREIGN PATENT DOCUMENTS

| | | |
|---|---|---|
| EP | 0 762 855 | 8/1999 |
| FR | 2 720 264 | 12/1995 |
| FR | 2 797 171 | 2/2001 |
| WO | WO01/10333 | 2/2001 |

* cited by examiner

*Primary Examiner*—Cary E. O'Connor
(74) *Attorney, Agent, or Firm*—Lilling & Lilling P.C.

(57) ABSTRACT

A dental implant which contains a bi-cortical anchor apparatus for insertion into a jawbone, the anchor apparatus including a tool receptor for interacting with a tool which facilitates insertion of the apparatus. An implant member arranged for insertion into a jawbone, the member containing a cervix to secure a dental prosthesis and a through conduit to support an anchor apparatus. A complementary system including an implant member and a template, the latter meshing with and helping align the implant member. A method for inserting the implant member into a bore in the jawbone. The method includes drilling a channel in the jawbone through a drill-bit guide channel and inserting a bi-cortical anchor apparatus through the channel and through a conduit of an implant member, anchoring at least two portions of the anchor apparatus.

28 Claims, 16 Drawing Sheets

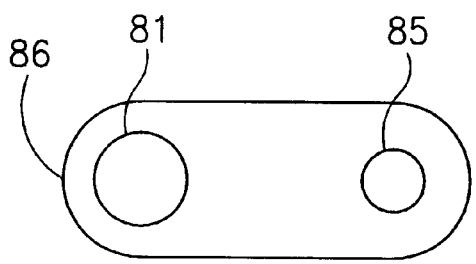
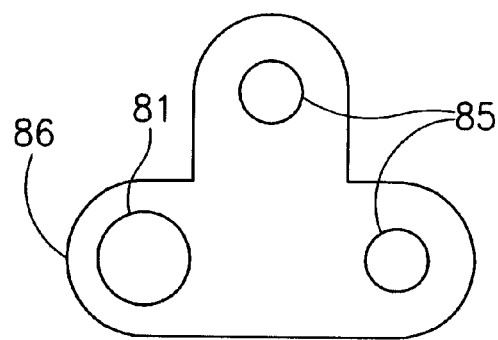
FIG.5B        FIG.5C
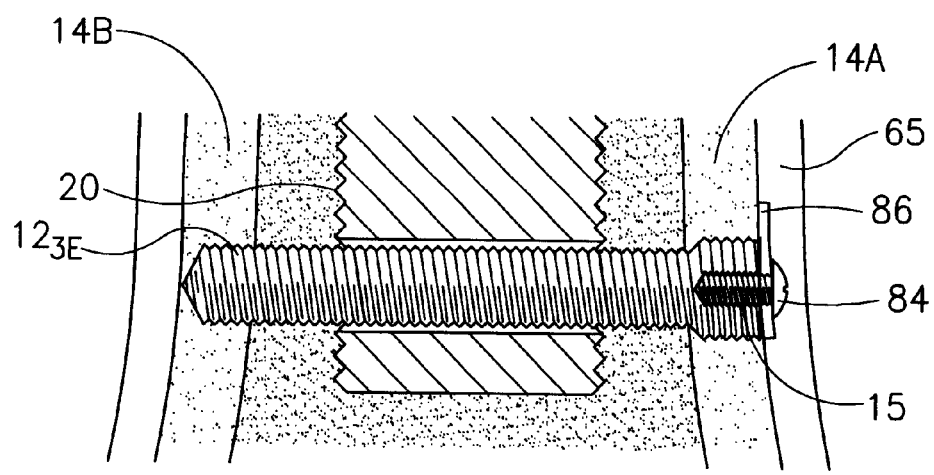
FIG.5D

BI-CORTICAL DENTAL IMPLANT

FIELD OF THE INVENTION

The present invention relates to a tooth replacement, which has an implant member, and to the forming thereof.

BACKGROUND OF THE INVENTION

Dental implants are known. Generally, the process of installing an implant is performed in two steps. During the first step, a bore is drilled vertically through the jawbone. The jawbone is formed of a hard, cortical exterior and a cancellous, sponge-like interior. In a sense, the jawbone can be envisioned as hard crest and side plates that encase the cancellous interior. The bore is drilled through the cortical crest and into the cancellous interior. A generally cylindrical implant member is fitted into the bore, so that its top portion reaches the bone crest. The cylindrical implant member may be a bullet-like cylinder, which has a smooth surface, and which is press-fitted into the bore. Alternatively, the cylindrical implant member may have screw threads around its external surface so as to self-tap its way into the bore. The implant member includes a support structure, for example, a threaded cervix, for supporting a dental prosthesis. During the first step, the cervix is sealed. The bone is then allowed to heal, as the cancellous interior grows around the implant. Often, the implant member is coated with a bone-growth enhancing material, to induce the healing process, which may take several months. During the second step, after healing, the sealant is removed from the support structure of the implant member, and a second member, a dental prosthesis having a crown, which serves as an artificial tooth, and a post, is secured onto the implant member. The post is preformed or cast individually, for example, as a threaded stud that substantially matches the threaded cervix of the implant member. The crown is then cemented onto the post.

A few of the factors, which determine the success of the implant, are as follows:

1. Depth of the bore: For good anchoring, a relatively deep bore of 10–16 mm is generally required. However, for some people, especially older people, a bore deeper than 5 or 6 mm on the lower jaw may make contact with the mandibular canal. For these people, good anchoring with respect to the cancellous bone tissue cannot be achieved.

2. Bacterial penetration: The penetration of bacteria poses additional risk to the bone tissue, and can also lead to local mortality and implant failure. Generally, when the bone heals around the implant member, and the gingival tissue closes on it, there is no bacterial penetration along the interface between the implant member and the bone. However, when the dental prosthesis is installed, the interface surface between the crown and the post, on the one hand, and the implant member support structure, such as the threaded cervix, on the other hand, is susceptible to bacterial penetration.

3. Trauma to the cancellous bone tissue: Excessive vertical or lateral forces by the implants on the cancellous bone tissue can lead to resorption, a phenomenon in which the density and mass of the cancellous tissue decreases, eroding support for the implant.

U.S. Pat. No. 5,611,688 to Hanosh describes a tooth replacement with an expanding implant member. The inserted, or distal portion of the implant member is arranged to expand outwardly into the surrounding cancellous bone.

U.S. Pat. No. 5,951,288 to Sawa describes a tooth replacement with an implant member formed of a shape-memory alloy which is maintained at a cool temperature for easy and non-traumatic insertion. Once in place, the implant member warms to body temperature and expands to anchor itself within the cancellous bone.

U.S. Pat. No. 6,015,294 to Lauks describes a tooth replacement with an implant member having a relatively short cylindrical section and a plurality of wedges extending from the distal portion of the cylindrical section and penetrating the cancellous bone.

These patents, while claiming to solve prior-art problems, still rely on anchoring of the implant member with respect to the cancellous bone, and are generally too deep for those people for whom there is a risk of contact with the mandibular canal or the sinus cavity.

U.S. Pat. No. 5,702,346 to Lazzara describes a tooth replacement with an implant member having a width that is substantially the same as the distance between the cortical plates at the site of installation, so that when the implant member is installed, it is anchored with respect to the cortical plates. However, in general, the bore in the bone is not symmetric, with respect to the two cortical plates, so it is nearly impossible for the center of the bore to be at equal distances from the two cortical plates. Therefore, there may be situations in which Lazzara's implant member is anchored only with respect to one cortical plate, causing an unbalanced load distribution. Furthermore, there may be sections of the bone where the cortical plates close in, and the distance between them narrows. These sections are called undercuts. If an implant member is forced passed undercuts, the cortical plates may crack or puncture.

U.S. Pat. No. 3,981,079 to Lencyzycki describes a tooth replacement wherein the implant member has at least one pre-formed partially threaded lateral channel and is anchored with respect to the buccal cortical plate with at least one lateral screw. The implant member may be hollow or solid. For example, the implant member may be a hollow cylinder, and the partially threaded lateral channel may be two orifices on opposite walls of the cylinder. The distal orifice, with respect to the operator and the buccal cortical plate, has an internal thread, and the proximal orifice has a smooth internal surface, but with a diameter that is slightly larger than that of the distal orifice. Generally, the lateral screw is threaded, self-tapping its way into a lateral channel in the buccal cortical plate and a portion of the cancellous bone tissue. The lateral screw passes freely through the proximal orifice and is threaded into the distal orifice. The lateral screw then advances into the bone, beyond the distal orifice, self-tapping its way through the cancellous bone tissue. Thus the lateral screw is anchored with respect to the buccal cortical plate and with respect to the distal, threaded orifice, but not with respect to the lingual cortical plate.

This arrangement suffers from several drawbacks. Anchoring the implant member with respect to only one cortical plate creates an unbalanced, asymmetric load distribution on the jawbone. In addition, since the cortical plates are wood-like, having little elasticity, the fact that the lateral screw is threaded into both the implant member and the buccal cortical plate prevents re-adjustment and settling of the implant member and may lead to cracking of the cortical plate. The desirable situation is that which maintains the implant member in place, while providing some elasticity for re-adjustment.

U.S. Pat. No. 5,797,741 to Bombard et al. describes a tooth replacement with a solid implant member having a lateral key, whose function is similar to that of the lateral screw in U.S. Pat. No. 3,981,079, hereinabove. In a first embodiment, the lateral key is smooth and cylindrical, for easy insertion, and is arranged to pass through lateral channels, drilled in advance in the jawbone, and through the implant member. The lateral key is thus anchored with respect to the two cortical plates, and load distribution is generally symmetric on the jawbone. However, the tooth replacement described by U.S. Pat. No. 5,797,741 is applicable to the anterior portion of the mouth and would be difficult to install in the posterior portion.

The use of a smooth lateral key has some additional drawbacks:

1. For its insertion, the lateral key is tapped with a mallet, from the buccal side, into the channel drilled in the buccal cortical plate, through the implant member, and into the channel drilled in the lingual cortical plate. The tapping may cause a crack or an incipient crack in the lingual cortical plate. Such a crack is unlikely to be detected; yet it may lead to a loss of stability for the implant.
2. To facilitate its insertion, the lateral key must be, slightly smaller than the lateral channels in the jawbone, giving the implant member a certain freedom of movement. Indeed, with time, the bone tissue will grow and surround the implant member and the lateral key. However, during the initial period, before bone growth occurs, implant movement and play can damage the cancellous bone tissue and cause resorption, resulting in implant failure.

In a second embodiment, the lateral key has a threaded distal end, with respect to the operator and the buccal cortical plate, and is arranged to pass through a lateral channel in the buccal cortical plate and the cancellous bone tissue and into a blind, internally threaded channel in the implant member. In essence, this arrangement is similar to that of U.S. Pat. No. 3,981,079, hereinabove, and suffers from similar drawbacks, namely, that anchoring the implant member with respect to only one cortical plate creates an unbalanced, asymmetric load distribution on the jawbone. The locking of the implant member with the buccal cortical plate may cause a pulling action towards the buccal cortical plate. Additionally, it prevents re-adjustment and settling of the implant member. It can also result in cracking of the buccal cortical plate.

Additionally, both U.S. Pat. Nos. 3,981,079 and 5,797,741 use templates which are supported by superstructures of their respective implant members, for drilling lateral channels through the jawbone. However, these templates are held in place by implant members that have not been anchored to the cortical plates and are fixed in place only by the cancellous bone tissue. Therefore, the templates themselves are subject to movement and play, which the soft, cancellous bone tissue permits. In consequence, the positioning afforded by these templates may be inaccurate, and a lateral screw or key may not slide easily into a lateral channel, as expected. Instead, its insertion may be traumatic to the patient, and may even lead to bone damage that can affect the success of the implants.

There are other patents which use lateral screws, anchored with respect to a cortical plate, to support an implant member, for example, U.S. Pat. Nos. 3,436,826 and 4,084,318.

SUMMARY OF THE INVENTION

It is an aim of the present invention to provide a tooth replacement, having an implant member, anchored with bi-cortical anchor apparatus that has been uniquely designed to provide optimum bi-cortical stability and retention. When an implant member is anchored bi-cortically, loads are transferred to the hard, cortical bone that provides it with primary stabilization—stabilization during the initial stage, before bone growth around the implant occurs. Additionally, an implant member anchored bi-cortically is capable of withstanding masticatory forces even in poor quality bones. Furthermore, because of the bi-cortical retention, an implant member that is inserted into the jawbone only to a depth of about 4–7 mm is possible, thus avoiding the mandibular canal. Bi-cortical retention may also be used for an implant member of greater depths, for example, 10–18 mm, when desired.

There is thus provided in accordance with a preferred embodiment of the present invention a bi-cortical anchor apparatus, arranged for insertion into a jawbone, from a proximal cortical plate towards a distal cortical plate. The bi-cortical anchor apparatus includes a distal portion, having a distal effective diameter and a distal surface which can bite into and engage with virgin tissue of the distal cortical plate, anchoring tightly to the plate. It also includes a mid portion, having a mid-portion effective diameter and a mid-portion surface which can support an implant member without locking. The apparatus further includes a proximal portion, having a proximal effective diameter, which is somewhat larger than both the distal and mid-portion effective diameters, and which has a proximal surface which can bite into and engage with virgin tissue of the proximal cortical plate, anchoring tightly to the plate. Finally, the apparatus includes a tool receptor at the proximal-most end of the proximal portion for interacting with a tool to facilitate the insertion of the apparatus.

There is further provided in accordance with a preferred embodiment of the present invention a bi-cortical anchor apparatus, arranged for insertion into a jawbone, from a proximal cortical plate towards a distal cortical plate. The bi-cortical anchor apparatus includes a distal portion, having a distal effective diameter and a distal surface, which can bite into and engage tissue of the distal cortical plate, anchoring tightly to the plate. The anchor apparatus further includes a mid portion, having a mid-portion effective diameter and a mid-portion surface, which can support an implant member without locking. The apparatus also includes a proximal portion, having a proximal effective diameter and a proximal surface which can bite into and engage a tissue of the proximal cortical plate, anchoring tightly to the plate. Finally, the anchor apparatus includes a tool receptor at the proximal-most end of the proximal portion for interacting with a tool to facilitate the insertion of the apparatus.

In yet another embodiment of the bi-cortical anchor apparatus, the distal portion, the mid portion and the proximal portion are machined as a single portion and have the same surface and the same effective diameter.

In another embodiment of the bi-cortical anchor apparatus, the mid portion includes a smooth surface.

In a further embodiment of the bi-cortical anchor apparatus, the proximal and distal effective diameters are substantially the same, and the mid portion effective diameter is somewhat smaller.

Additionally, in an embodiment of the bi-cortical anchor apparatus, the distal surface, which can bite into and engage with the tissue or virgin tissue of the distal cortical plate, anchoring tightly to the plate, has a threaded surface having at least one complete revolution.

In an embodiment of the invention, the proximal surface of the bi-cortical anchor apparatus bites into and engages the tissue or virgin tissue of the proximal cortical plate, anchoring it tightly to the plate. The proximal surface is a threaded surface having at least one complete revolution.

In another embodiment of the bi-cortical anchor apparatus, the distal surface bites into and engages with the tissue or virgin tissue of the distal cortical plate, anchoring it tightly to the plate. The distal surface is a tapping tool surface. In yet another embodiment, the proximal surface is a tapping tool surface.

In yet another embodiment of the bi-cortical anchor apparatus, the anchor apparatus completely penetrates the distal cortical plate while anchoring into the plate, so as to be flush with the external surface of the distal cortical plate.

In still another embodiment of the bi-cortical anchor apparatus, the anchor apparatus partially penetrates the distal cortical plate, while anchoring into the plate.

Another embodiment of the bi-cortical anchor apparatus has the anchor apparatus arranged for insertion so as to be flush with the external surface of the proximal cortical plate.

Additionally, in another embodiment of the bi-cortical anchor apparatus, the apparatus further includes a head at the proximal-most end, external to the proximal cortical plate, where the head includes the tool receptor.

In yet another embodiment, the tool receptor of the bi-cortical anchor apparatus is arranged to interact with a tool selected from a group which consists of an Ellen key, a screwdriver and a wrench.

Another embodiment of the bi-cortical anchor apparatus, includes a tool receptor which is a threaded internal cervix arranged to interact with a tool. The tool has proximal and distal portions with respect to the operator and a threaded surface at the distal portion which complements the threaded internal cervix. The tool has a finger-gripping portion at the proximal portion and a stem, connecting the proximal and distal portions, whereby the tool can guide the apparatus through a template drill-bit guide channel.

In another embodiment, the tool receptor of the bi-cortical anchor apparatus is arranged to interact with a tool, which can guide the apparatus through a template drill-bit guide channel.

Another embodiment of the bi-cortical anchor apparatus can come in various lengths to accommodate jawbones of different widths.

In yet another embodiment, the bi-cortical anchor apparatus can come in a range of effective diameters, the effective diameters selected from a group which consists of the distal effective diameter, the mid-portion effective diameter and the proximal effective diameter.

A further embodiment of the bi-cortical anchor apparatus includes a gradual increase in the diameter between the mid-portion and proximal effective diameters.

There is additionally provided in accordance with a preferred embodiment of the present invention an implant member arranged for insertion into a jawbone along a vertical axis of a tooth. The implant member includes near and far portions and a cervix, at the near portion, arranged so as to secure a dental prosthesis. The member also includes a through conduit, at the far portion, arranged to support a bi-cortical anchor apparatus, without locking. The conduit is separated from the cervix with a solid barrier which acts as a bacteria barrier. The member includes a bi-cortical anchor apparatus, arranged for insertion into a jawbone, from a proximal cortical plate towards a distal cortical plate. The bi-cortical anchor apparatus includes a distal portion, having a distal effective diameter and a distal surface, which can bite into and engage with virgin tissue of the distal cortical plate, anchoring tightly to the plate. The bi-cortical apparatus also includes a mid portion, having a mid-portion effective diameter and a mid-portion surface, which can support an implant member without locking. The apparatus includes a proximal portion, having a proximal effective diameter, which is somewhat larger than both the distal and mid-portion effective diameters. The proximal portion has a proximal surface which can bite into and engage virgin tissue of the proximal cortical plate, anchoring tightly to the plate. Finally the apparatus has a tool receptor, at the proximal-most end of the proximal portion, for interacting with a tool, to facilitate the insertion of the apparatus.

Also provided, in accordance with a preferred embodiment of the present invention is an implant member, arranged for insertion into a jawbone. The implant member includes near and far portions, and a cervix, at the near portion, arranged to secure a dental prosthesis. The implant member further includes a through conduit, at the far portion, arranged to support a bi-cortical anchor apparatus without locking. The through conduit is separated from the cervix with a solid barrier, which acts as a bacteria barrier. The bi-cortical anchor apparatus is arranged for insertion into a jawbone, from a proximal cortical plate towards a distal cortical plate. The bi-cortical anchor apparatus includes a distal portion, having a distal effective diameter and a distal surface, which can bite into and engage with a tissue of the distal cortical plate, anchoring tightly to the plate. The anchor apparatus further includes a mid portion, having a mid-portion effective diameter and a mid-portion surface, which can support an implant member without locking. The anchor apparatus also includes a proximal portion, having a proximal effective diameter and a proximal surface which can bite into and engage with a tissue of the proximal cortical plate, anchoring tightly to the plate. Finally, the anchor apparatus includes a tool receptor, at the proximal-most end of the proximal portion, for interacting with a tool, to facilitate the insertion of the apparatus.

In yet another embodiment, the through conduit of the implant member has a smooth internal surface. In still another embodiment, the implant member defines a z-axis along the vertical axis of the tooth, an x-axis, in any one of the buccal to lingual and buccal to palatal directions, and a y-axis, perpendicular to the x- and z-axes. The through conduit is slanted with respect to an axis selected from a group which consists of the x-, y-, and z-axes, Additionally, in an embodiment of the invention, the through conduit of the implant member is an open through conduit.

In an embodiment of the invention, the implant member is arranged for insertion to a depth in a range between 4 and 18 mm. In another embodiment, it is arranged for insertion to a depth of 5 to 7 mm.

In another embodiment of the invention, the implant member further includes a threaded external surface for self-tapping an internal thread into the bone tissue during insertion.

In yet another embodiment, the implant member is arranged as a maxillary implant member which reaches into the sinus cavity.

Additionally, in another embodiment, the implant member further includes a mini-plate to increase the anchoring of the bi-cortical anchor apparatus to the proximal cortical plate.

In another embodiment, the implant member further includes at least one screw to increase the anchoring of the mini-plate to the proximal cortical plate.

The implant member in another embodiment of the present invention further includes a complementary template for guiding a drill bit from the proximal cortical plate into the through conduit.

There is also provided, in accordance with a preferred embodiment of the present invention, a complementary system, which includes an implant member having a portion which protrudes from the jawbone, when the implant member is installed in the jawbone. The implant member also has a through conduit at a far portion with respect to an operator, invisible to the operator, when the implant member is installed in the jawbone. The complementary system also has a template, having a distal vertical section, running generally along a distal cortical plate of the jawbone, so as to press against the distal cortical plate. The template also has a proximal vertical section, running generally along a proximal cortical plate of the jawbone. The proximal vertical section includes a drill-bit-channel housing and a drill-bit guide channel, located within the drill-bit-channel housing. The template also includes a lateral section, arranged to mesh with the portion of the implant member which protrudes from the jawbone, thereby aligning the drill-bit guide channel with the through conduit of the implant member.

In another embodiment of the present invention, the drill-bit guide channel of the complementary system guides the bi-cortical anchor apparatus for insertion into the jawbone.

In yet another embodiment of the complementary system, the portion which protrudes from the jawbone is a mount that is provided with the implant member.

Additionally, in another embodiment of a complementary system according to the present invention, the portion, which protrudes from the jawbone is a superstructure of the implant member.

In yet another embodiment of a complementary system, the system further includes a slide mechanism for adjusting to jawbones of different widths.

In an embodiment of a complementary system according to the present invention, the system further includes at least one spike arranged for piercing a cortical plate selected from a group which consists of the distal cortical plate and the proximal cortical plate, for increasing the hold on the jawbone. In some systems, the at least one spike is a plurality of spikes.

In yet another embodiment of a complementary system according to the present invention, the drill-bit-channel housing is formed as a hollow bolt, arranged to selectably press against the proximal cortical plate.

In a further embodiment of the present invention, the drill-bit guide channel of a complementary system is located within the hollow bolt, and further guides the bi-cortical anchor apparatus for insertion into the jawbone.

Additionally, in another embodiment of a complementary system according to the present invention, the distal vertical section runs generally along the distal cortical plate of the jawbone, the section pressing against the plate. The distal vertical section is a leaf spring.

Yet another embodiment of a complementary system further includes a ratchet which is arranged to clamp the template and the distal cortical plate. The distal vertical section runs generally along the distal cortical plate of the jawbone, pressing against it and acting as a distal prong of the ratchet. In yet another embodiment, the ratchet further includes a locking mechanism arranged for jawbones of different widths.

In other embodiments of a complementary system, the ratchet is a three-prong ratchet, having two proximal prongs, to the left and to the right of the drill-bit guide channel housing, along the y-axis, and having a single distal prong.

In embodiments of the present invention, the implant member of the complementary system is constructed in one of the ways described above.

There is also provided, in accordance with a preferred embodiment of the present invention, a method of installing an implant member which includes the steps of drilling a bore from the bone crest into the jawbone and inserting an implant member, having a through conduit, into the bore. The method then includes positioning a template, while meshing a lateral section of the template with a portion of the implant member which protrudes from the jaw, thus aligning a drill-bit guide channel with the through conduit of the implant member. This is followed by drilling a channel in the jawbone, through the drill-bit guide channel of the template and inserting a bi-cortical anchor apparatus from the proximal cortical plate through the bone channel and then through a conduit of the implant member, towards the distal cortical plate, for bi-cortical retention, while self-tapping an internal thread in the bone channel. Anchoring the distal portion of the bi-cortical anchor apparatus thus is effected by biting into tissue of the distal cortical plate, engaging the plate. The method also includes the step of anchoring the proximal portion of the bi-cortical anchor apparatus by biting into tissue of the proximal cortical plate and engaging that plate.

In a further embodiment of the present invention, a method is provided where the step of positioning further includes the step of pressing a hollow bolt, which houses the drill-bit guide channel, against the proximal cortical plate.

Yet another embodiment of the present invention provides a method where the step of inserting the bi-cortical anchor apparatus further includes the step of inserting through the drill-bit guide channel without moving the template. This step occurs between the step of drilling a channel in the jawbone and the step of inserting the bi-cortical anchor apparatus.

In still another embodiment of the present invention, a method is provided where clamping the jawbone between proximal and distal vertical sections of a template further includes clamping between a proximal vertical section of the template and at least one distal leaf spring.

Additionally, in another embodiment of the present invention, a method is provided where clamping the jawbone between proximal and distal vertical sections of a template further includes clamping with a ratchet.

Another embodiment of the present invention provides a method where clamping the jawbone between proximal and distal vertical sections of a template further includes piercing at least one cortical plate with spikes.

Yet another embodiment of the present invention provides a method which further includes the step of employing a mini-plate to increase the anchoring of the bi-cortical anchor apparatus to the proximal cortical plate.

In still another embodiment of the present invention, a method is provided where drilling a bore from the bone crest into the jawbone further includes drilling a bore from bone crest into the sinus cavity.

In another embodiment of the present invention, a method is provided which further includes employing a mini-plate to increase the anchoring of the bi-cortical anchor apparatus to the proximal cortical plate.

Another embodiment of the present invention provides a method which further includes employing at least one screw to increase the anchoring of the mini-plate to the proximal cortical plate.

In yet another embodiment of the present invention, a method is provided which further includes adjusting to jawbones of different widths.

BRIEF DESCRIPTION OF THE DRAWINGS

The present invention will be more clearly understood from the accompanying detailed description and drawings, in which same number designations are maintained throughout the figures for similar elements and in which:

FIGS. 5B and 5C illustrate mini-plates that may be used with an implant member in accordance with an embodiment of the present invention;

FIG. 5D shows a schematic illustration of a cortical anchor apparatus further anchored with a mini-plate and a screw in accordance with the present invention;

DETAILED DESCRIPTION OF THE PREFERRED EMBODIMENT

Figure 1A:
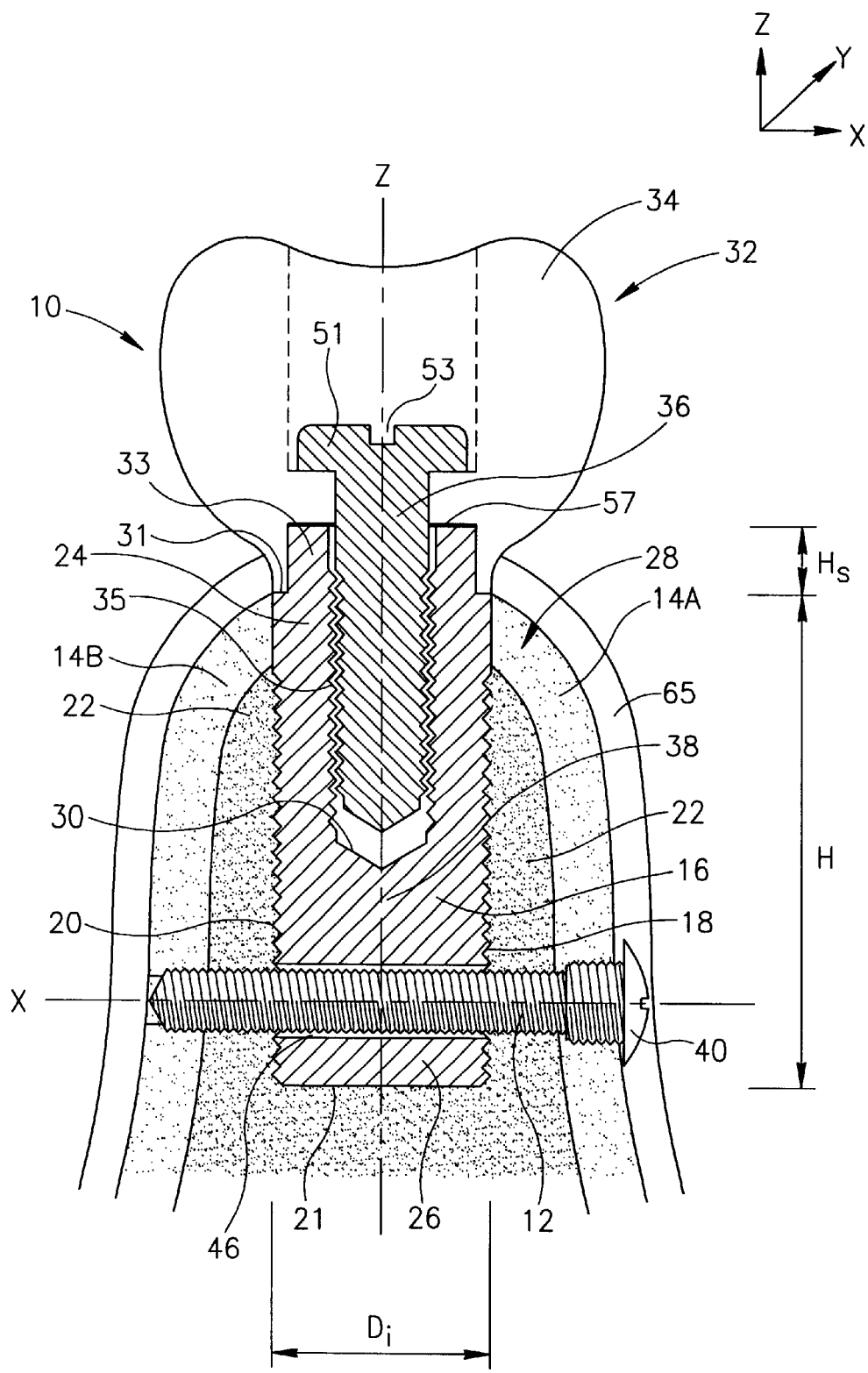
FIGS. 1A and 1B schematically illustrate a tooth replacement having an implant member anchored with a bi-cortical anchor apparatus in accordance with an embodiment of the present invention.
Figure 1B:
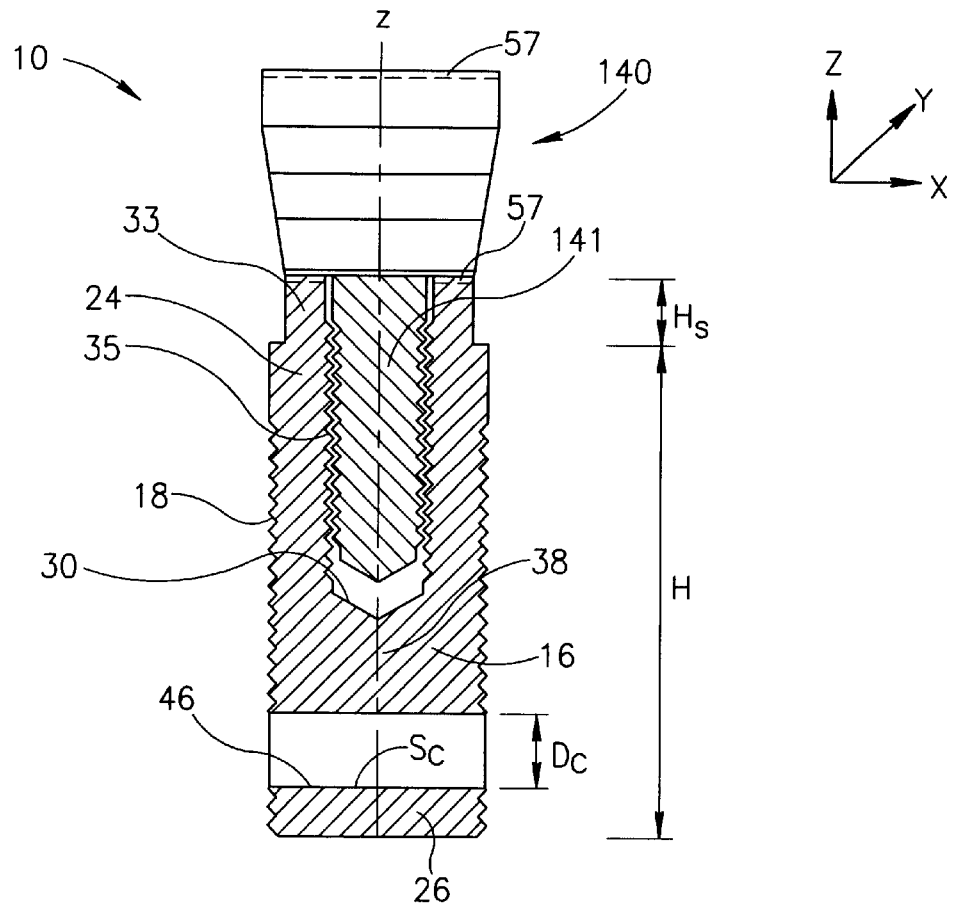
Figure 1B:
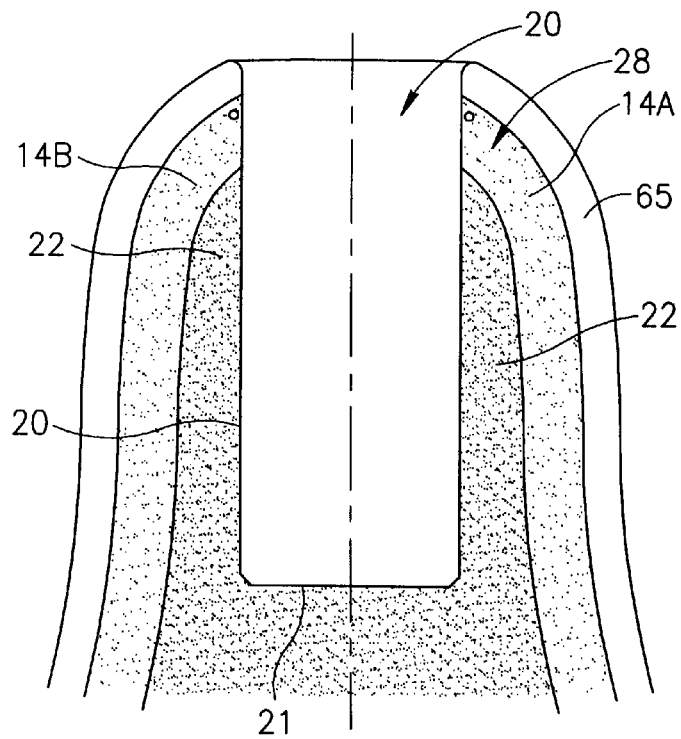

Reference is made to FIGS. 1A and 1B, which schematically illustrate a tooth replacement 10, having an implant member 16, anchored with bi-cortical anchor apparatus 12, which has been uniquely designed to provide bi-cortical retention, in accordance with the present invention. FIG. 1A illustrates tooth replacement 10 in the jawbone and FIG. 1B illustrates the jawbone and an implant member 16, just prior to insertion.

The jawbone defines a z-axis along the vertical axis of the tooth, an x-axis, in the buccal to lingual direction, and a y-axis, perpendicular to both. In the following description, the z direction is regarded as a vertical direction, and the x-y plane is regarded as a lateral plane. Near and far describe positions with respect to the operator along the z-axis, while proximal and distal describe positions with respect to the operator along the x-axis.

Implant member 16, for example, a solid cylinder, is arranged for insertion into a bore 20, drilled in the z direction, from a crest 28 of the jawbone, at a near side of the jawbone, into a cancellous interior 22 of the jawbone, to a bore far end 21. Preferably, an external surface 18 of implant member 16 is threaded, to increase the surface area in contact with cancellous bone tissue 22, so as to increase the support of the bone tissue around implant member 16. Preferably, implant member 16 is screwed into bore 20 with some force, so as to self-tap its way into bore 20 and carve an internal thread in cancellous bone tissue 22, so as to ensure a tight fit and provide primary implant support. Alternatively, external surface 18 may be a smooth surface and implant member 16 may be press-fitted into bore 20. In alternate embodiments of the invention, implant member 16 may have a polygonal rather than a cylindrical cross-section, or have another external surface structure. Implant member 16 has a near portion 24 and a far portion 26.

Implant member 16 is arranged for supporting a: dental prosthesis 32, which has a crown 34 and a post 36. Preferably, implant member 16 includes, at near portion 24, a cervix 30, which preferably includes an internal thread and is arranged for supporting post 36, which preferably includes an external thread that complements the internal thread of cervix 30. Alternatively, another known locking mechanism may be used between near portion 24 of implant member 16 and dental prosthesis 32.

Preferably, depth H of bore 20 and of the portion of implant member 16 inserted into bore 20 is about 4–7 mm. However, the present invention is equally applicable to deeper implants, for example, of 10–18 mm. Preferably, a diameter $D_i$ of bore 20 is about 4–6 mm. Bores of other diameters are also possible; however, it is desirable that the bore diameter be smaller than the lateral distance between the two cortical plates at any point along bore 20.

In a preferred embodiment of the present invention, implant member 16 may include a superstructure 33, to augment its length. While implant member 16 is inserted into the jawbone, to depth H, superstructure 33 remains above bone crest 28, and fits into crown 34 of dental prosthesis 32, to a height $H_S$. The purpose of superstructure 33 is to augment the length of cervix 30 into which post 36 is fitted, while maintaining depth H short, for example 6 mm. When the depth H is long, for example 10–18 mm, superstructure 33 need not be used. Superstructure 33, which generally has a hexagonal shape, is technically known as an external hexagon.

Preferably, a head 51 of post 36 includes a notch 53 or a slit 53, arranged for a tool (not shown), for example, a screwdriver, in order to screw post 36 into implant 16. Alternatively, head 51 has a polygon shape, and may be screwed into post 36 with a wrench. Alternatively, another known locking mechanism between implant member 16 and post 36 may be used.

At far portion 26, implant member 16 includes a support structure 46, such as a through conduit 46, which has a preferably smooth internal surface $S_C$ and an internal diameter $D_C$. Implant member 16 may further include an alignment indicator 57 such as a carved slit 57, or another mark, at its nearest surface, which is visible to the operator, wherein indicator 57 is aligned with conduit 46, to give the operator an indication of the alignment of conduit 46, which is invisible to him.

In accordance with the present invention, implant member 16 is anchored to the jawbone with bi-cortical anchor apparatus 12 (FIG. 1A), which has been uniquely designed to provide optimum bi-cortical stability and retention.

FIG. 1B further illustrates a mount 140, with which implant member 16 is provided. Mount 140 is used for inserting implant member 16 into bore 20 and includes a threaded post 141, fitted into cervix 30. Mount 140 may further include an alignment indicator (not shown), such as a carved slit or another mark, on its nearest surface, visible to the operator. Indicator 57 is aligned with conduit 46, which is invisible to the operator. After insertion, mount 140 and threaded post 141 are removed, and cervix 30 is sealed.

Figure 2A:
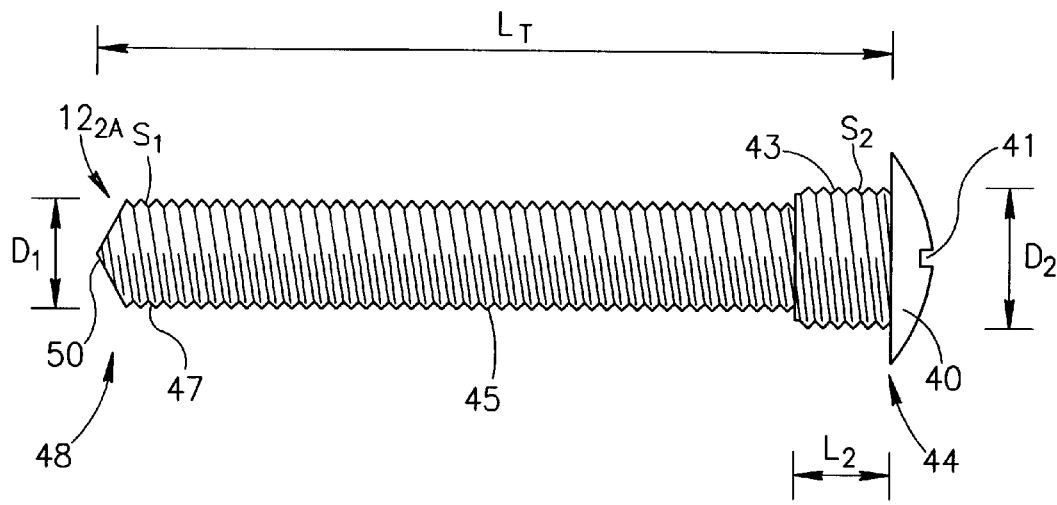
FIG. 2A schematically illustrates an embodiment of a bi-cortical anchor apparatus in accordance with an embodiment of the present invention.

Reference is now made to FIG. 2A, which schematically illustrates an embodiment of bi-cortical anchor apparatus 12, such as bi-cortical anchor apparatus $12_{2A}$ in accordance with the present invention. Preferably, bi-cortical anchor apparatus $12_{2A}$ is formed as a screw, having proximal and distal ends 44 and 48, with respect to the operator, a total length $L_T$, a tip 50 at distal end 48, and a notch 41 at proximal end 44. Bi-cortical anchor apparatus 12 may further include a head 40. Preferably, bi-cortical anchor apparatus $12_{2A}$ is arranged for insertion into a jawbone, from buccal cortical plate 14A (FIG. 1A) towards lingual cortical plate 14B, so that when inserted, head 40, remains external to the jawbone, resting against buccal cortical plate 14A. In time, head 40 is enclosed by gingival tissue 65 (FIG. 1A). Notch 41 serves as a tool receptor, for interacting, for example, with a screwdriver tip (not shown) or an Ellen key (not shown), to facilitate the insertion of bi-cortical anchor apparatus $12_{2A}$.

Bi-cortical anchor apparatus $12_{2A}$ includes:
a distal portion 47, of a distal effective diameter $D_1$, having a distal surface $S_1$, which is preferably threaded, and which is operable to bite into and engage with virgin tissue of lingual cortical plate 14B (FIG. 1A), and anchor tightly, thereto;
a mid portion 45, which is preferably machined as an integral part with distal portion 47, so as to have the same effective diameter and surface as distal portion 47, and which is operable to support dental implant 16 (FIG. 1A) without locking thereto; and
a proximal portion 43, of a length $L_2$, and of a proximal effective diameter $D_2$, which is somewhat larger than distal effective diameter $D_1$, and which has a proximal surface $S_2$, preferably threaded, operable to bite into and engage with virgin tissue of buccal cortical plate 14A (FIG. 1A), and anchor tightly, thereto.

The effective diameter of the threaded surfaces refers to the maximum diameter of the threaded surface.

Figure 2B:
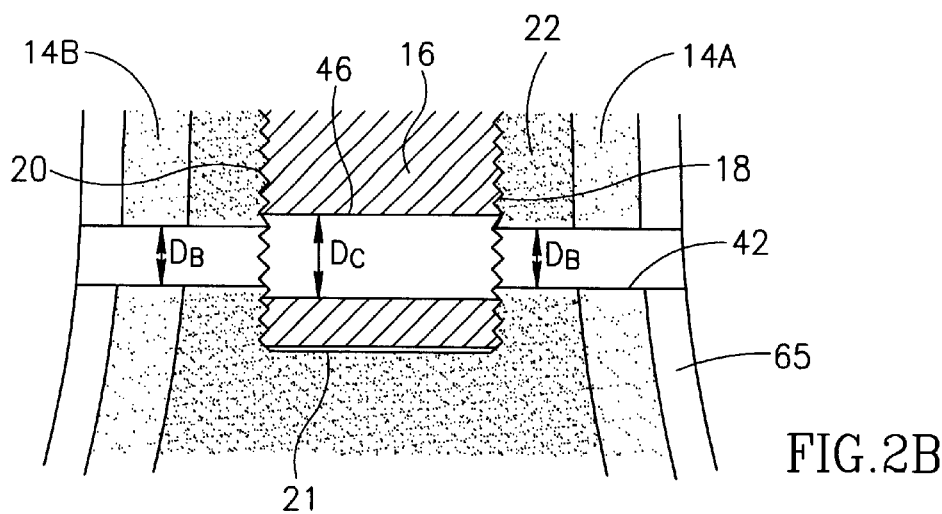
FIG. 2B schematically illustrates a section of the jawbone and implant member in a bore in accordance with an embodiment of the present invention.

Reference is now made to FIG. 2B, which schematically illustrates a section of the jawbone, showing buccal and lingual cortical plates 14A and 14B, cancellous bone tissue 22, and implant member 16 in bore 20, in accordance with the present invention. Implant member 16 includes through conduit 46, having preferably smooth internal surface $S_C$ (FIG. 1B) and internal diameter $D_C$. The jawbone includes a channel 42, preferably drilled along the x-axis, from buccal cortical plate 14A towards lingual cortical plate 14B, as will be described hereinbelow, in conjunction with FIGS. 6A-10. Channel 42 has a diameter $D_B$ and may be a through channel or may reach only to conduit 46 of implant member 16.

Figure 2C:
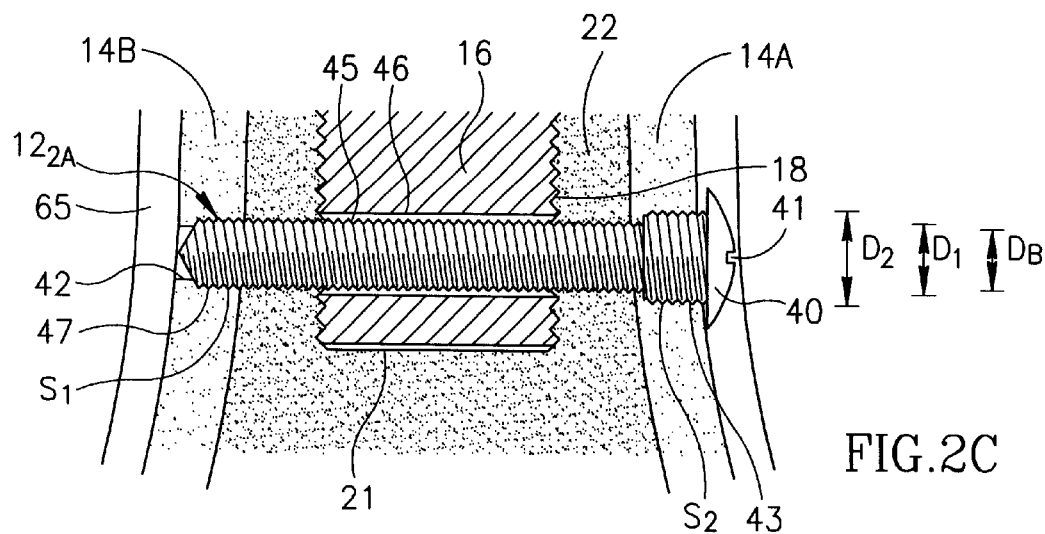
FIG. 2C schematically illustrates a bi-cortical anchor apparatus after insertion into the jawbone of FIG. 2B in accordance with an embodiment of the present invention.

Reference is now made to FIG. 2C, which schematically illustrates bi-cortical anchor apparatus $12_{2A}$ after insertion into the jawbone of FIG. 2B, from buccal cortical plate 14A to lingual cortical plate 14B, in accordance with the present invention. Diameter $D_B$ of channel 42 is smaller than both diameters $D_1$ and $D_2$ of bi-cortical anchor apparatus $12_{2A}$; therefore, the insertion of bi-cortical anchor apparatus $12_{2A}$ into channel 42 involves a screwing motion, in which bi-cortical anchor apparatus $12_{2A}$ self taps its way into channel 42, carving a thread in virgin tissue of the jawbone.

The main features that provide bi-cortical anchor apparatus $12_{2A}$ with optimum bi-cortical retention are surfaces $S_1$ and $S_2$, operative to bite into and engage with the cortical bone tissue so as to anchor with respect to it, the diametric increase from $D_1$ to $D_2$, and the screwing, self-tapping motion. The importance of these features is as follows:

1. Anchoring with respect to lingual cortical plate 14B: since distal effective diameter $D_1$ of distal portion 47 is somewhat larger than diameter $D_B$ of bone channel 42, as bi-cortical anchor apparatus $12_{2A}$ self taps its way in channel 42, towards lingual cortical plate 14B, threaded surface $S_1$ of distal portion 47 bites into and engages with virgin bone tissue, which has not been tampered with during drilling, so as to provide anchoring with respect to lingual cortical plate 14B without clearance and play.

2. Anchoring with respect to buccal cortical plate 14A: since proximal effective diameter $D_2$ of proximal portion 43 is somewhat larger than diameter $D_1$, it bites into and engages with virgin bone tissue at buccal cortical plate 14A, which has not been tampered with and weakened by the passage of portions 47 and 45 through it, so as to provide anchoring with respect to buccal cortical plate 14A without clearance and play. Preferably anchoring includes anchoring by at least two thread revolutions of threaded surface $S_2$; thus, length $L_2$ of section 43 is preferably long enough to include at least two complete thread revolutions. Alternatively, one thread revolution may be used.

As both section 43 and 47 are tightly anchored with respect to virgin cortical bone tissue, in a manner that eliminates clearance and play, optimum bi-cortical retention of implant member 16 is achieved. Tight anchoring is particularly important for primary stabilization of the implant and for resisting immediate loading during the implant initial stage, before bone growth around the implant occurs.

In accordance with a preferred embodiment of the present invention, mid portion 45, which also includes threaded surface $S_1$, is similarly anchored with respect to cancellous bone tissue 22 along its sections outside conduit 46 of implant member 16, so as to further increase the tight anchor and the primary stabilization of implant member 16.

Now also referring to FIG. 2A, in accordance with the preferred embodiment of the present invention, total length $L_T$ of bi-cortical anchor apparatus $12_{2A}$ is substantially the same as the width of the jawbone at the location of the implant, so as to completely penetrate the jawbone. In time, tip 50 is enclosed by gingival tissue 65.

Preferably, bi-cortical anchor apparatus $12_{2A}$ is provided in a variety of lengths $L_T$, for example, in steps of 1 mm, to accommodate jawbones of different widths. Alternatively, bi-cortical anchor apparatus $12_{2A}$ may be provided in steps of 0.75 mm, or 0.5 mm, to provide a greater range of lengths.

However, in accordance with the present invention, when an exact match with the jawbone width cannot be found from amongst the available lengths $L_T$, it is recommended that the operator select bi-cortical anchor apparatus $12_{2A}$ of length $L_T$ that is smaller than the jawbone width, preferably by no more than 1 mm. Since the cortical plates are about 2 mm in thickness, bi-cortical anchor apparatus $12_{2A}$ of length $L_T$, smaller that the jawbone width by no more than 1 mm, will partially penetrate the lingual cortical plate, to a depth of about 1 mm. In accordance with the preferred embodiment of the present invention, length $L_T$ is smaller than the jawbone width by no more than 0.5 mm, so as to partially penetrate the lingual cortical plate to a depth of about 1.5 mm.

In accordance with the preferred embodiment of the present invention, sufficient anchoring of a threaded surface against a cortical plate occurs when the threaded surface is anchored by at least one complete thread revolution, and preferably, two complete thread revolutions. Thus, in accordance with the preferred embodiment of the present invention, bi-cortical anchor apparatus $12_{2A}$ will be provided in a range of lengths $L_T$ that will ensure two compete thread revolutions into lingual cortical plate 14B, even for partial penetration of cortical plate 14B. Additionally, a length $L_2$ of proximal portion 43 is determined as at least the length of two complete thread revolutions.

Reference is now made to FIGS. 3A–3E which schematically illustrate several designs of bi-cortical anchor apparatus 12, in accordance with alternative embodiments of the present invention.

Figure 3A:
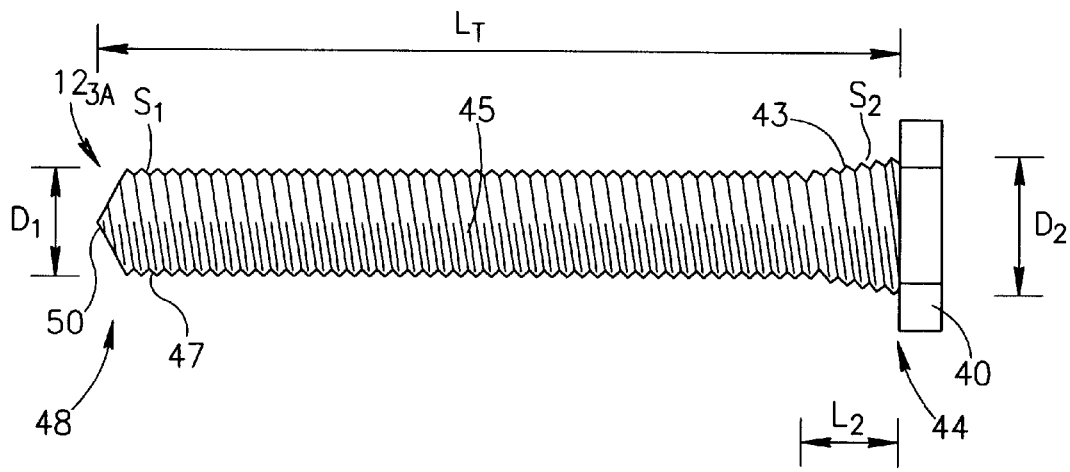
FIGS. 3A–3E schematically illustrate several bi-cortical anchor apparatus designs in accordance with alternative embodiments of the present invention.

FIG. 3A illustrates bi-cortical anchor apparatus $12_{3A}$ having a distal effective diameter $D_1$ and a maximum proximal effective diameter $D_2$, wherein the change in diameters is gradual over length $L_2$.

Figure 3B:
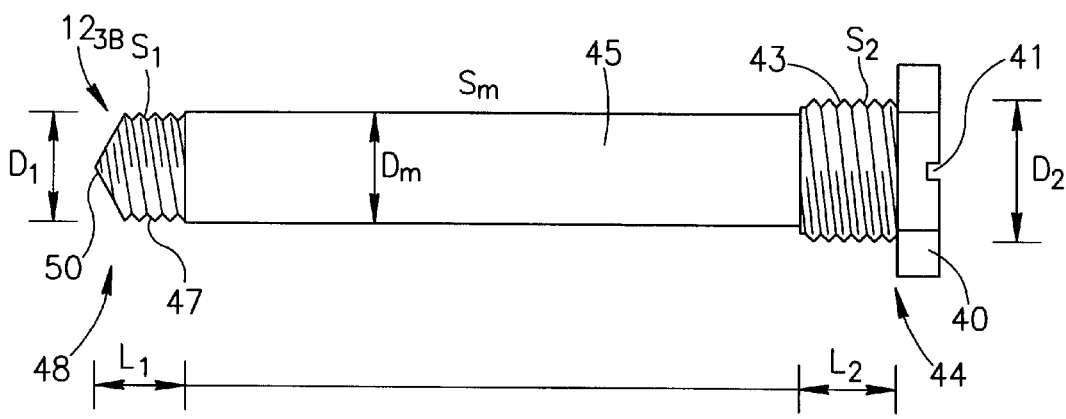

FIG. 3B illustrates bi-cortical anchor apparatus $12_{3B}$ of which distal portion 47 includes threaded surface $S_1$, while mid portion 45 has a smooth surface $S_m$. As a consequence of the machining of distal portion 47, its effective diameter $D_1$ is somewhat smaller than a diameter $D_m$ of smooth mid portion 45. Length $L_1$ of distal portion 47 is determined as at least the length of two complete thread revolutions of effective diameter $D_1$.

Figure 3C:
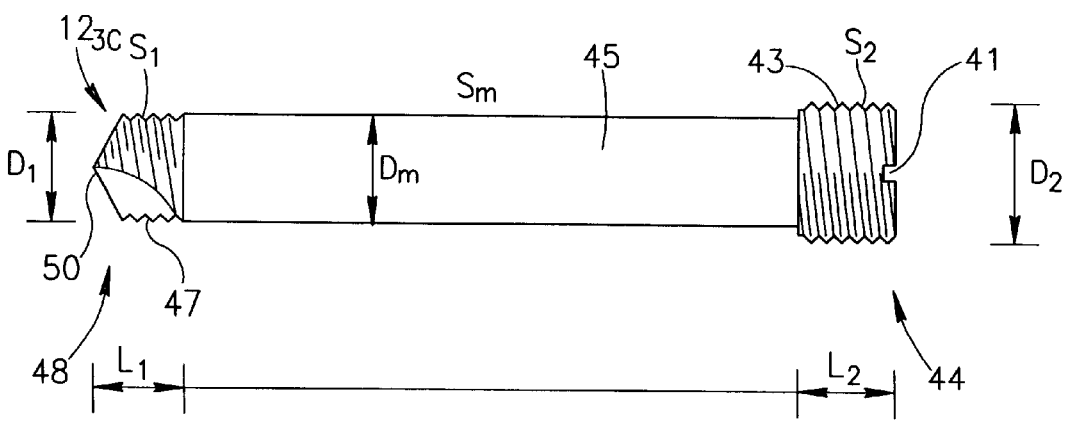

FIG. 3C illustrates bi-cortical anchor apparatus $12_{3C}$ for which surface $S_1$ of distal portion 47 is a tapping tool surface, and effective diameter $D_1$ is the maximum diameter of the tapping tool surface.

Figure 3D:
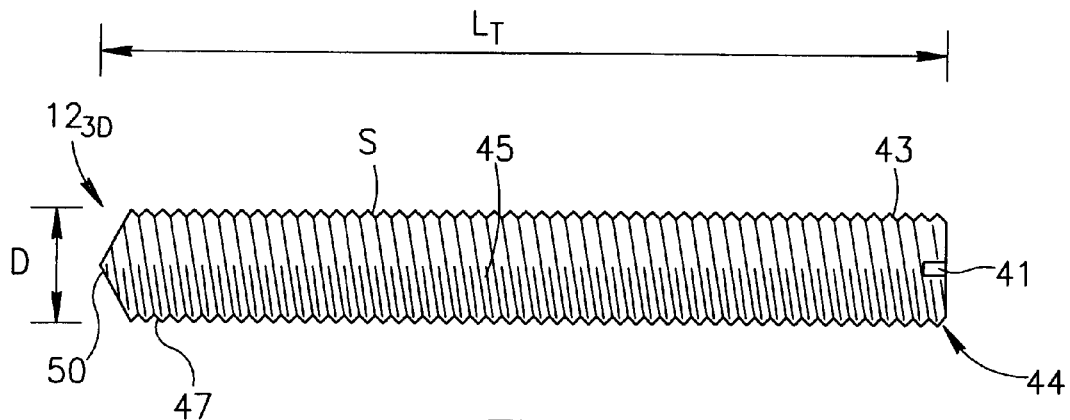

FIG. 3D illustrates bi-cortical anchor apparatus $12_{3D}$, having a single diameter D throughout, and a single, preferably threaded surface S, throughout. This embodiment, while simple, still provides proximal and distal surfaces that are operable to bite into and engage with cortical plates 14A and 14B.

Figure 3E:
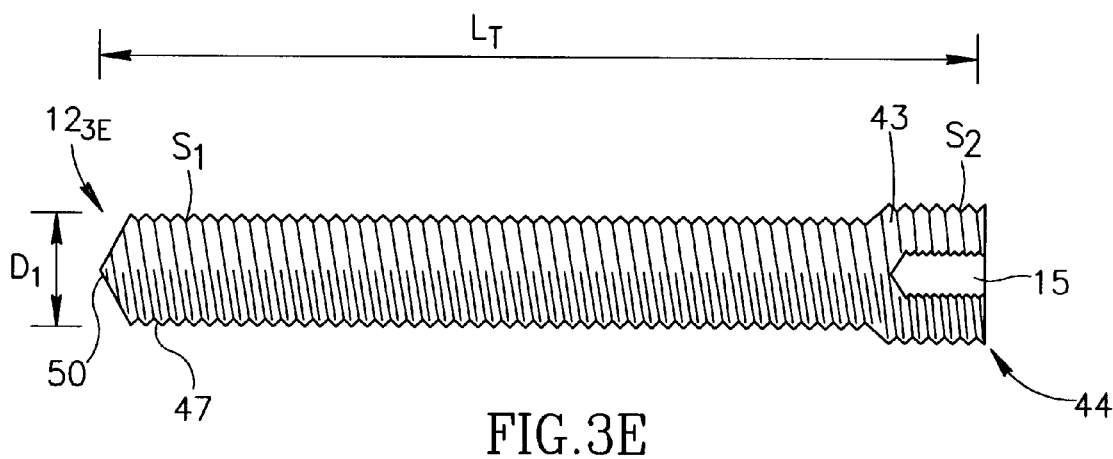

In accordance with the preferred embodiment of the present invention, FIG. 3E illustrates bi-cortical anchor apparatus $12_{3E}$, similar in construction to the bi-cortical anchor apparatus $12_{2A}$ (FIG. 2A), but having no screw head and including an internal, threaded cervix 15 at proximal end 44, in place of notch 41.

FIGS. 3A–3D also illustrate alternative designs to proximal end 44.

As seen in FIG. 3A, head 40 may itself serve as the tool receptor, being shaped for example, as a polygon, arranged to interact with a wrench (not shown).

Alternatively, as seen in FIG. 3B, head 40 may be shaped as a polygon, arranged to interact with a wrench, and include notch 41, arranged to interact with a screwdriver tip (not shown) or an Ellen key (not shown), providing the operator with more than one tool receptor, and giving him the flexibility to choose the most appropriate tool. The choice of an appropriate tool may depend on the location of the implant in the mouth.

Alternatively, as seen in FIGS. 3C–3D, bi-cortical anchor apparatus $12_{3C}$ and $12_{3D}$ have no screw heads and are arranged to be flush with the external surface of buccal cortical plate 14A. For each, proximal portion 43 includes notch 41, which serves as the tool receptor, for interacting with a screwdriver tip (not shown), an Ellen key (not shown), or both. Bi-cortical anchor apparatus $12_{3C}$ or $12_{3D}$ may be inserted into the bone, for example with a screw driver, through a template drill-bit guide channel, using any of the templates described hereinbelow, in conjunction with FIGS. 6A–10.

Alternatively, as seen in FIG. 3E, illustrating the preferred embodiment of the present invention, bi-cortical anchor apparatus $12_{3E}$ has no screw head, but includes a threaded, internal cervix 15, arranged to interact with a special tool 17, described hereinbelow, in conjunction with FIG. 3F.

Figure 3F:
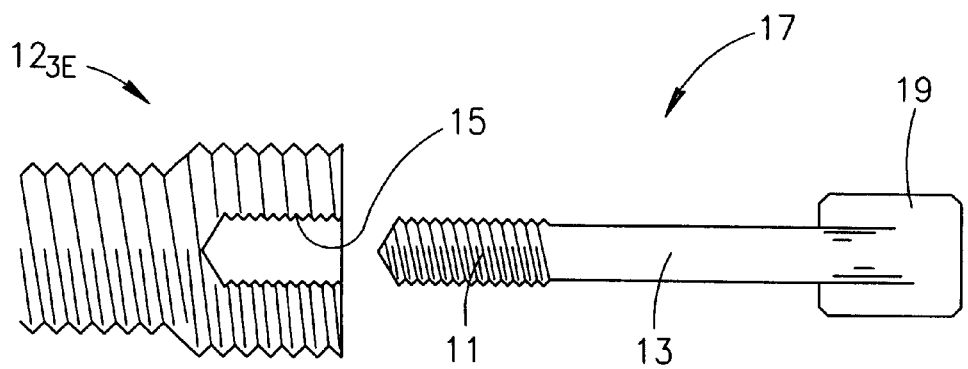
FIG. 3F shows a special tool in accordance with the preferred embodiment of the present invention.

Reference is now made to FIG. 3F, which describes special tool 17, in accordance with the preferred embodiment of the present invention. Tool 17 includes a threaded surface at a distal portion 11, which complements threaded internal cervix 15 of bi-cortical anchor apparatus $12_{3E}$. Additionally, tool 17 includes a stem 13 and a proximal, finger-gripping portion 19. Bi-cortical anchor apparatus $12_{3E}$ may be inserted into the bone, with tool 17, through a template drill-bit guide channel, using any of the templates described hereinbelow, in conjunction with FIGS. 6A–10.

Reference is again made to FIG. 1A, for further examination of tooth replacement 10.

In accordance with the present invention, a solid barrier 38 separates bi-cortical anchor apparatus 12 at far portion 26 from cervix 30 at near portion 24, to prevent bacterial penetration from the mouth to reach bi-cortical anchor apparatus 12 and thereafter, cancellous bone tissue 22. Bacterial penetration can lead to local mortality of bone tissue and implant failure. If the bone is allowed to heal around implant member 16 so that gingival tissue 65 closes on it, there is little risk of bacterial penetration along implant external surface 18. However, when dental prosthesis 32 is installed, penetration of bacteria along an interface surface 31 between dental prosthesis 32 and implant member 16 and along an interface 35 between post 36 and cervix 30 can take place. Since these interfaces are between two non-organic biocompatible materials, such as metals, ceramics or plastics, which are not susceptible to bacterial attack, there is no harm in such bacterial penetration. However, if cervix 30 of near portion 24 reached down as far as through conduit 46 of far portion 26, bacteria could infiltrate through conduit 46 and move along it to cancellous bone tissue 22 and also to cortical plates 14A and 14B. Solid barrier 38, which prevents such an attack, is an essential feature of the present invention.

In accordance with the invention, implant member 16 may include more than one through conduit 46 and may be supported by more than one bi-cortical anchor apparatus 12.

In accordance with the present invention, through conduit 46, bone channel 42 (FIG. 2B) and bi-cortical anchor apparatus 12 may be slanted with respect to either the x- and y-axes, the z-axis, or all axes, in order to increase the thickness of cortical plates 14A and 14B and of cancellous bone tissue 22 that serve to anchor bi-cortical anchor apparatus 12.

Figure 4:
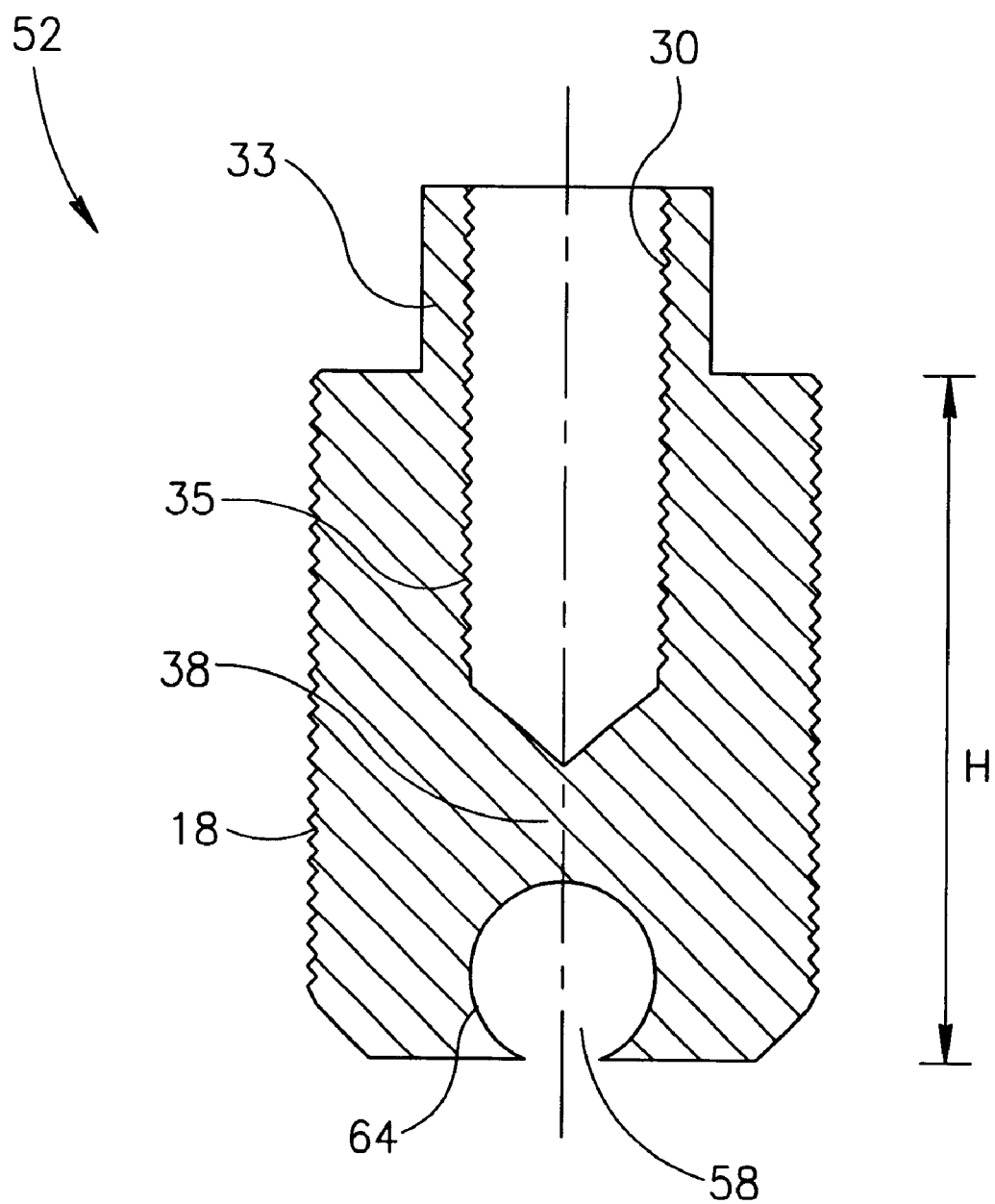
FIG. 4 schematically illustrates an implant member in accordance with an alternative embodiment of the present invention.

Reference is now made to FIG. 4, which schematically illustrates an implant member 52, in accordance with an alternative embodiment of the present invention. Implant member 52 includes an open through conduit 58, arranged to be supported by bi-cortical anchor apparatus 12. Open through conduit 58 has a cross-sectional arch 64, which is at least 180° and preferably 270° or more. The main advantage of open through conduit 58 is that the length of implant member 52, H, may be shorter than that of implant member 16 (FIG. 1A), while still maintaining bacterial barrier 38. Additionally, cancellous tissue bone growth around bi-cortical anchor apparatus 12, which happens with time, increases its stability.

Figure 5A:
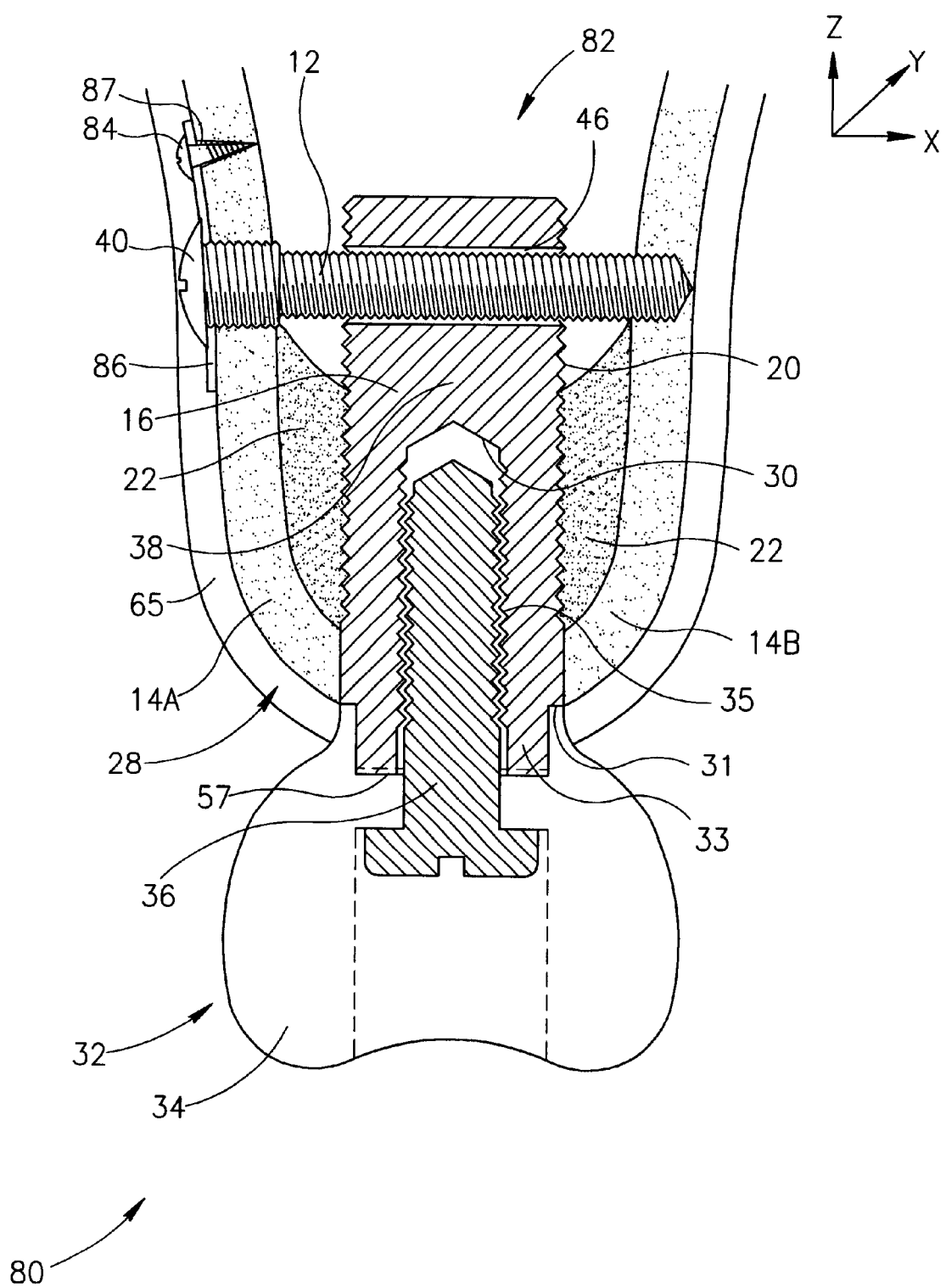
FIG. 5A schematically illustrates a maxillary tooth replacement through a sinus cavity anchored with a bi-cortical anchor apparatus in accordance with an alternative embodiment of the present invention.

Reference is now made to FIG. 5A, which schematically illustrates a maxillary tooth replacement 80, through a sinus cavity 82, anchored with bi-cortical anchor apparatus 12, in accordance with an alternative embodiment of the present invention.

In general, during the first step of drilling bore 20 through the jawbone, dentists avoid contact with sinus cavity 82. However, it is a well-known fact in the field of maxillofacial surgery, that when using mini-plates and screws for fixation, screws are sometimes inserted into buccal cortical plate 14A of sinus cavity 82. The screws may remain there for a long time, even indefinitely, without complication. Therefore, screws, supported by mini-plates, into buccal cortical plate 14A of the sinus cavity 82 may similarly be used to stabilize tooth replacement 80, so that even where there is little bone support for tooth replacement 80, implant loads can be transferred onto strong buccal and lingual cortical plates 14A and 14B. The risk of infection is minimal, since with time gingival tissue 65 covers the mini-plate 86 and screws 84 and prevents bacterial penetration from the oral cavity.

Reference is now also made to FIGS. 5B and 5C which illustrate mini-plates that may be used with implant member 80, in accordance with the present invention. The reason for the mini-plate 80 is that, in general at the sinus area, the cortical plate tends to be rather thin and weak. Preferably, a mini-plate 86, having a hole 81, may be used as a washer between head 40 (FIG. 5A) and buccal cortical plate 14A, to further strengthen the cortical support to tooth replacement 80.

Furthermore, mini-plate 86 may include at least one additional screw hole 85 arranged for inserting at least one additional screw 84 into buccal cortical plate 14A. Preferably, after bi-cortical anchor apparatus 12 is inserted into the jawbone, at least one additional lateral channel 87, of a diameter slightly smaller than screw 84, is drilled from mini-plate hole 85 into buccal cortical plate 14A. At least one screw 84 is then inserted, into buccal cortical plate 14A, preferably self-tapping an internal thread into buccal cortical plate 14A.

Mini-plate 86 may be arranged for one or more screws 84, having one or more holes 85. Holes 85 may be at the same elevation with respect to bone crest 28 (FIG. 5A) or at different elevations. Similarly, hole 81 and holes 85 may be at the same elevation with respect to bone crest 28 or at different elevations.

In accordance with the present invention, mini-plate 86 and at least one screw 84 may be used also with the embodiment depicted in FIG. 1A.

Reference is now made to FIG. 5D which schematically illustrates cortical anchor apparatus 123E (FIG. 3E), further anchored with mini-plate 86 and screw 84, wherein screw 84 is fitted into internal cervix 15, in accordance with the present invention. The advantage of this arrangement is that bi-cortical anchor apparatus $12_{3E}$ may be inserted via a template drill-bit guide channel, using any of the templates described hereinbelow, in conjunction with FIGS. 6A–10, yet it may be anchored to cortical plate 14A, with mini-plate 86, even though it does not have a screw head.

Figure 6A:
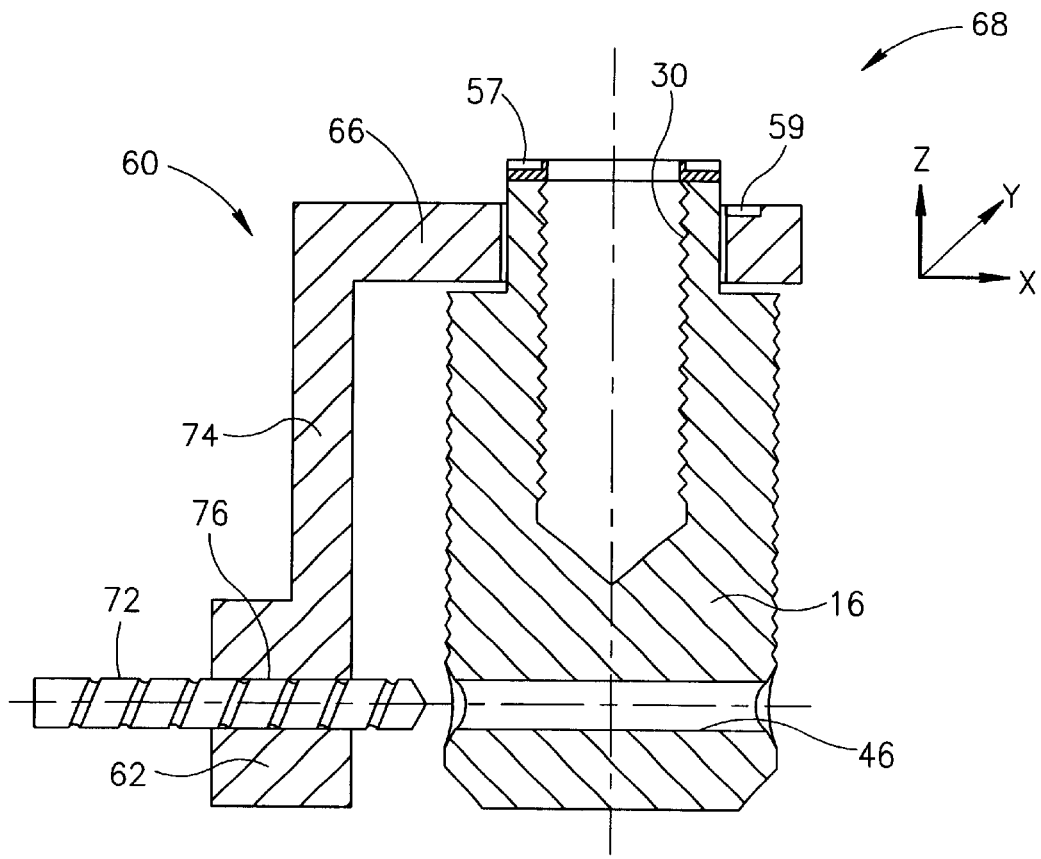
FIG. 6A schematically illustrates a complementary system including a template and an implant member in accordance with a template embodiment of the present invention.

Reference is now made to FIG. 6A, which schematically illustrates a complementary system of template and implant member 16 having a template 60, operative to guide a drill bit 72, into through conduit 46 of implant member 16, in order to drill bone channel 42 (FIG. 2B), in accordance with a first template embodiment of the present invention. Since through conduit 46 of implant member 16 is not visible to the operator, once implant member 16 has been inserted into bore 20 (FIG. 1B), a guiding template is needed to drill bone channel 42 towards through conduit 46.

Template 60 includes a lateral section 66, generally parallel with the x- and y-axes, arranged to mesh with a portion of implant member 16, which protrudes from the jawbone, such as superstructure 33 (FIG. 1A) or mount 140 (FIG. 1B). Additionally, template 60 includes a proximal vertical section 74, for running generally along buccal cortical plate 14A. Proximal vertical section 74 includes a drill-bit-channel housing 62 and a drill-bit guide channel 76, located within housing 62. When template 60 is meshed with implant member 16, with lateral section 66 meshed with superstructure 33 (FIG. 1A) or mount 140 (FIG. 1B), drill bit 72 inserted into drill-bit guide channel 76 will be aligned with through conduit 46 of implant member 16. Drill bit 72 may then be used to drill bone channel 42.

In accordance with some embodiments of the present invention, after it is used for drilling bone channel 42, template 60 is removed. Cortical anchor apparatus 12 is then inserted into bone channel 42, using an insertion tool (not shown), such as a screwdriver, a wrench, or an Ellen key.

However, in accordance with the preferred embodiment of the present invention, after it is used for guiding a drill bit into bone channel 42, and while still meshed with dental implant 16, template 60 may be further used to guide cortical anchor apparatus 12, such as cortical anchor apparatus $12_{3C}$, $12_{3D}$, or $12_{3E}$ (FIGS. 3C–3E) into the bone. Cortical anchor apparatus 12 may be guided by any tool having a stem, for example, a screw driver, an Ellen key, or tool 17 (FIG. 3F), fitted into drill-bit guide channel 76. After insertion and anchoring by biting into cortical anchor plates 14B and 14A, cortical anchor apparatus $12_{3E}$ may be further anchored to buccal cortical plate 14A with mini-plate 86 and screw 84, as shown hereinabove, in conjunction with FIG. 5D.

Figure 6B:
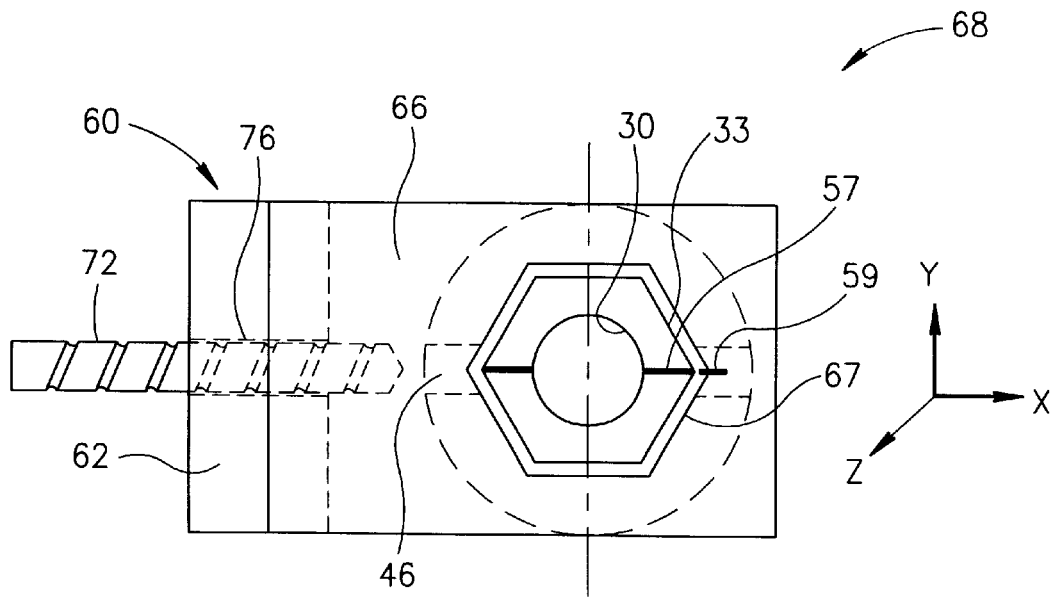
FIG. 6B schematically illustrates a top view of a complementary system showing a template and an implant member in accordance with an embodiment of the present invention.

Reference is now made to FIG. 6B, which schematically illustrates a top view of complementary system 68 showing template 60 and implant member 16, wherein lateral section 66 is meshed with superstructure 33 which is formed as an external hexagon 33, in accordance with the present invention. Preferably, lateral section 66 includes a cutout section 67 of generally the same hexagonal shape as superstructure 33, arranged to fit over it. Preferably, lateral section 66 further includes an alignment indicator 59, which is visible to the operator. When indicator 59 of template 60 and indicator 57 of implant member 16 are at a predetermined configuration, with respect to each other, drill-bit guide channel 76 is aligned with through conduit 46. Alternatively, lateral section 66 may be meshed with mount 140 (FIG. 1B), in place of superstructure 33.

In alternative embodiments of the present invention, superstructure 33 (FIG. 1A) or mount 140 (FIG. 1B), and cutout section 67 may be shaped as complementary polygons other than hexagons, or may have different complementary shapes altogether, for example, elliptical or round. In alternative embodiments of the present invention, a "carved-out" section 67 that is not a through cutout may replace cutout section 67. "Carved-out" section 67 may be fitted over a portion of implant member 16 that protrudes from the jawbone, like a hat. In alternative embodiments of the present invention, the complementary shapes of superstructure 33 or mount 140 and cutout section 67 define the alignment of template 60 with respect to implant member 16, and alignment indicator 59 is not necessary.

Figure 6C:
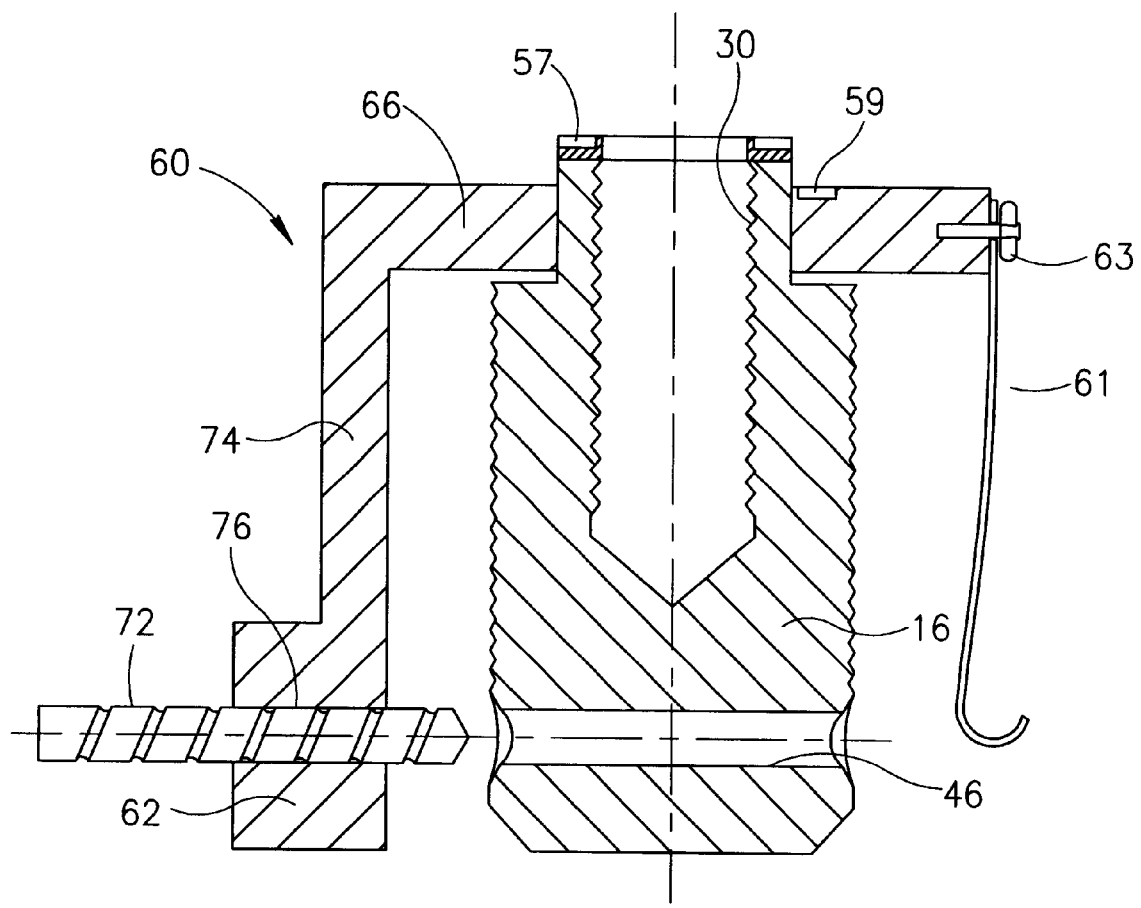
FIG. 6C schematically illustrates an alternative embodiment of a template in accordance with another embodiment of the present invention.

Reference is now made to FIG. 6C, which schematically illustrates an alternative embodiment of template 60, in accordance with the present invention. Template 60 may further include at least one leaf spring 61, running in a vertical direction, forming a distal vertical section 61. Preferably leaf spring 61 is attached to lateral section 66 and is operative to press against the lingual cortical plate 14B, as proximal vertical section 74 is arranged against buccal cortical plate 14A, so as to clamp the jawbone, thus increasing the stability of template 60. Preferably, a hinge 63 provides leaf spring 61 with rotational motion, generally in the y-z plane, to allow the operator to first position proximal vertical section 74 against buccal cortical plate 14A, and then lower leaf spring 61 so as to press against lingual cortical plate 14B.

The method of installing implant member 16, using template 60 includes the following steps (see also FIG. 1A):
1. drilling a bore 20 from bone crest 28, into the jawbone, along the z-axis;
2. inserting implant member 16 into bore 20, to a predetermined depth, H, preferably, with a screwing, self-tapping motion, which cuts an internal thread into cancellous bone tissue 22;
3. aligning indicator 57 of implant member 16 so that through conduit 46 runs in a desired direction;
4. meshing lateral section 66 of template 60 (FIGS. 6A–6C) with a portion of implant member 16 that protrudes from the jawbone and positioning proximal vertical section 74 against buccal cortical plate 14A, so that drill-bit guide channel 76 and drill bit 72 are aligned with through conduit 46 of implant member 16;
5. alternatively or additionally with step 4, aligning indicator 59 of template 60 with indicator 57 of implant member 16, to align drill-bit guide channel 76 and drill bit 72 with through conduit 46;
6. where leaf spring 61, forming distal vertical section 61, is used, positioning leaf spring 61 against lingual cortical plate 14B, to further stabilize template 60; and
7. drilling channel 42 into the jawbone (FIG. 2B). In accordance with the preferred embodiment of the present invention, the method of installing implant member 16, using template 60 proceeds as follows:
8. without moving template 60, inserting cortical anchor apparatus 12$_{3E}$ (FIG. 3E), through drill-bit guide channel 76 of template 60, with the help of a tool such as a screw driver or tool 17 (FIG. 3F);
9. anchoring surface $S_1$ of distal portion 47 with respect to lingual cortical plate 14B, by biting into and engaging thereto, and anchoring surface $S_2$ of proximal portion 43 with respect to buccal cortical plate 14A, by biting into and engaging thereto; and
10. removing template 60; and
11. where desired, positioning mini-plate 86 (FIG. 5D) against buccal cortical plate 14A, and anchoring it with screw 84.

It should be pointed out that the feature of the preferred embodiment of the present invention, of inserting the bi-cortical anchor apparatus 12 through drill-bit guide channel 76, without moving template 60 between bone channel 42 and inserting bi-cortical anchor apparatus 12, gives it a unique advantage over the prior art, as it greatly increases the precision of inserting bi-cortical anchor apparatus 12 into conduit 46 of implant member 16, and it minimizes trauma to the bone.

Alternatively, the method of installing implant member 16, using template 60 proceeds as follows:
8A. removing template 60;
9A. where desired, positioning mini-plate 86 (FIG. 5C) against buccal cortical plate 14A, with hole 81 (FIG. 5B) next to channel 42 (FIG. 2B);
10A. inserting bi-cortical anchor apparatus 12$_{2A}$ (FIG. 2A), from buccal cortical plate 14A, through bone channel 42 and conduit 46 of implant member 16, towards lingual cortical plate 14B, for bi-cortical retention, while self-tapping an internal thread in channel 42 of the bone;
11A. anchoring surface $S_1$ of distal portion 47 with respect to lingual cortical plate 14B, by biting into and engaging thereto, and anchoring surface $S_2$ of proximal portion 43 with respect to buccal cortical plate 14A, by biting into and engaging thereto; and
12A. where mini-plate 86 (FIG. 5C) is used, preferably stabilizing it further, with at least one screw 84.

Figure 7A:
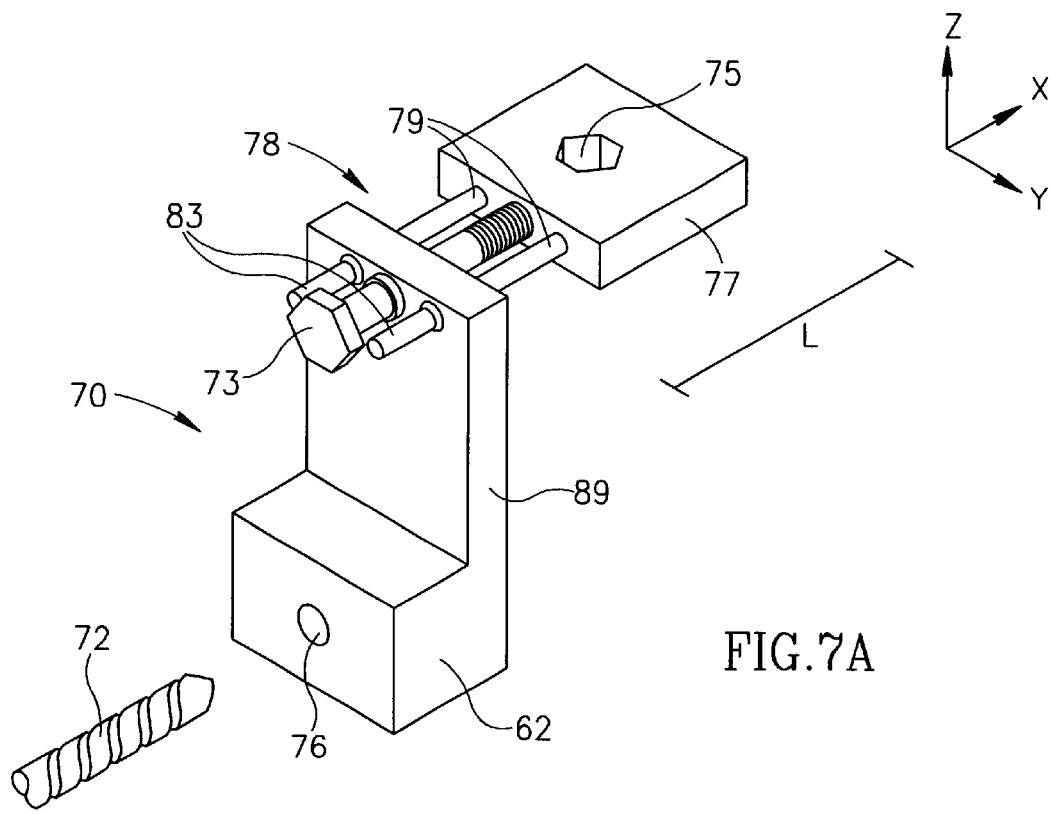
FIG. 7A schematically illustrates a mechanical template in accordance with another template embodiment of the present invention.

Reference is now made to FIG. 7A, which schematically illustrates a mechanical template 70, arranged for adjusting to jawbones of different widths, in accordance with a second template embodiment of the present invention. Template 70 includes a lateral section 77, having a cutout 75, or a "carved-out" section 75, arranged to mesh with a portion of implant member 16, which protrudes from the jawbone, such as superstructure 33 (FIG. 1A) or mount 140 (FIG. 1B). Additionally, template 70 includes a proximal vertical section 89, for running generally along buccal cortical plate 14A. Proximal vertical section 89 includes drill-bit channel housing 62 and drill-bit guide channel 76. When lateral section 77 is meshed with superstructure 33 (FIG. 1A) or mount 140 (FIG. 1B), drill-bit guide channel 76 is aligned with through conduit 46 of implant member 16.

Template 70 includes a sliding mechanism 78, which includes for example, at least two rods 79 that protrude from lateral section 77, along the x-axis, towards buccal cortical plate 14A. At least two rods 79 are arranged to slide in and out of holes 83 of proximal vertical section 89, in order to maintain lateral section 77 and proximal vertical section 89 perpendicular to each other, while selectably increasing or decreasing a length L, adjusting it to jawbones of different widths.

Additionally, template 70 may include a bolt 73, arranged to be selectably screwed into and out of a lateral section 77, along the x-axis, to control the increase and decrease in length L of lateral section 77. Alternatively, bolt 73 and a single rod 79 may be used.

In alternative embodiments, template 70 may further include leaf spring 61 (FIG. 6C), attached to lateral section 77, preferably with hinge 63, forming a distal vertical section 61, operative to press against lingual cortical plate 14B.

Figure 7B:
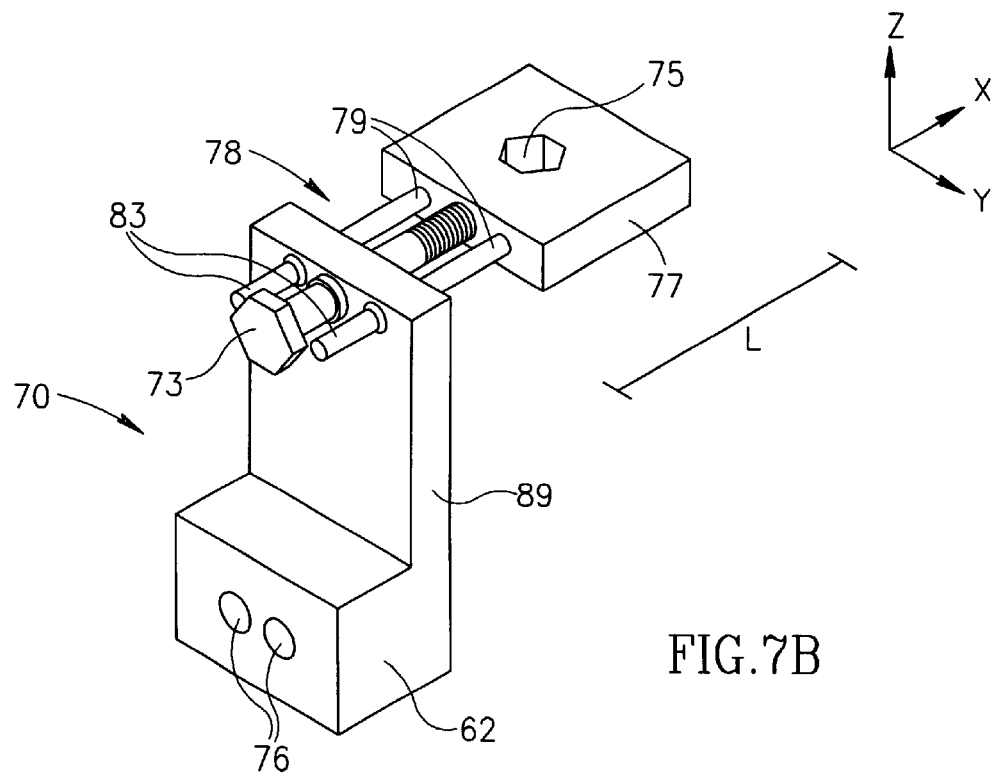
FIG. 7B is a schematic illustration of an alternative embodiment of a template having two or more drill-bit guide channels in accordance with the present invention.

Reference is now made to FIG. 7B, which schematically illustrates an alternative embodiment of template 70, having two or more drill-bit guide channels 76 in housing 62, in accordance with the present invention. The present embodiment is used for the insertion of two or more bi-cortical anchor apparatus 12 into implant members with two or more through conduits 46 (FIG. 1A). The two or more channels 76 may be at a same z value, that is at a same elevation, or at different elevations.

The method of installing implant member 16, using template 70 is similar to that of using template 60 described hereinabove, in conjunction with (FIGS. 6A–6C) but includes a step of adjusting template 70 to the width of the jawbone, using sliding mechanism 78 and bolt 73.

Figure 8:
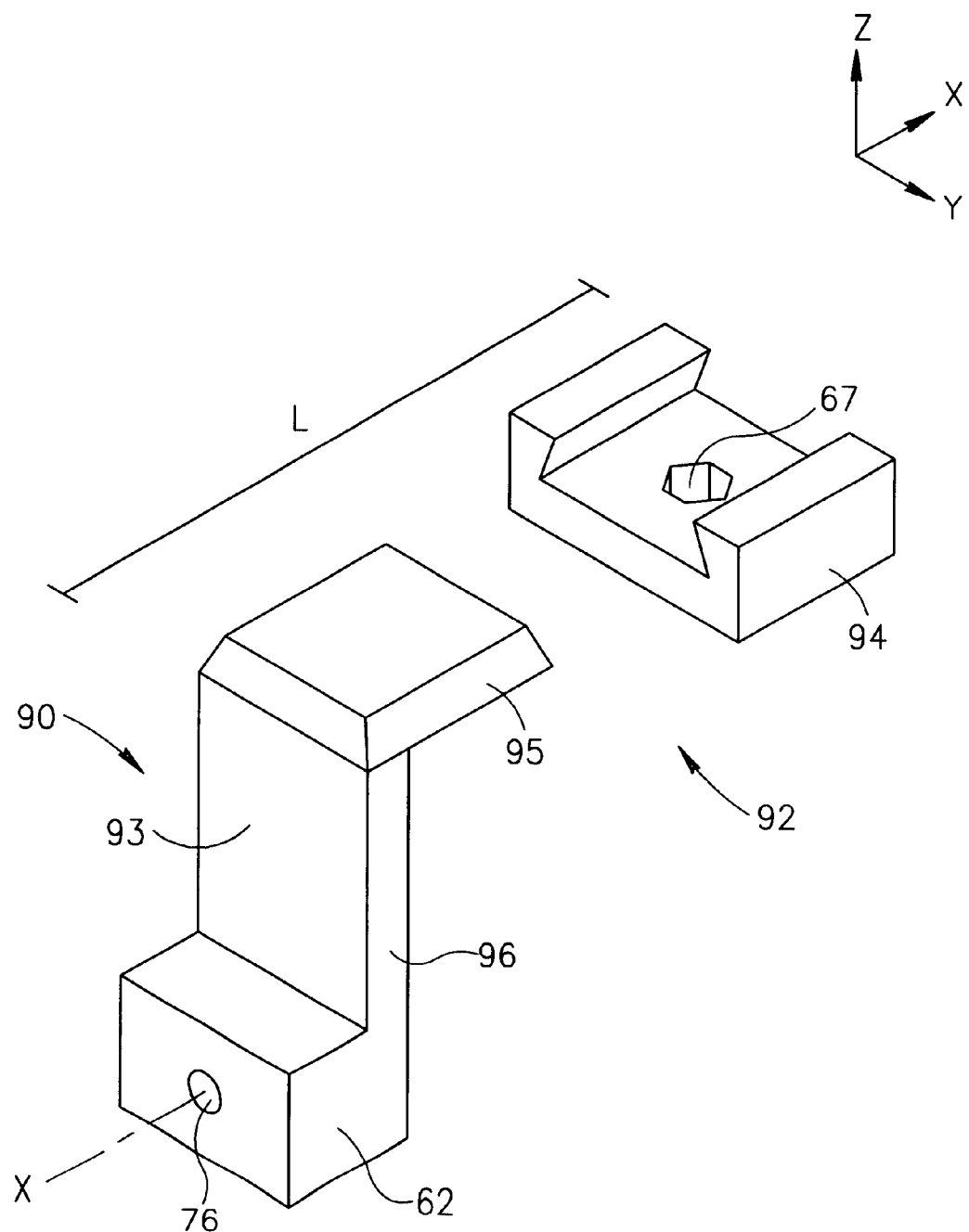
FIG. 8 is a schematic illustration of a template with a sliding mechanism in accordance with yet another template embodiment of the present invention.

Reference is now made to FIG. 8, which schematically illustrates a template 90 with a sliding mechanism 92, for adjusting to jawbones of different widths, in accordance with a third template embodiment of the present invention. Template 90 includes a first component 94, which is lateral and which has a cutout section 67, or a "carved out" section 67, arranged to mesh with a portion of implant member 16, which protrudes from the jawbone, such as superstructure 33 (FIG. 1A) or mount 140 (FIG. 1B).

Template 90 further includes a second component 96, having a lateral portion 95, arranged to fit into lateral component 94, via sliding mechanism 92, to selectably increase or decrease length L. Second component 96 further includes a proximal vertical section 93, which includes drill-bit-channel housing 62 and drill-bit guide channel 76, for guiding drill bit 72 (FIG. 6A).

For forming slide mechanism 92, lateral component 94 and lateral portion 95 may be shaped as complementary puzzle pieces, in the y-z plane, so that lateral portion 95 may slide within lateral component 94, along the x direction, but be prevented from motion in the y and z directions.

Templates 90 may further include leaf spring 61 (FIG. 6C), attached to lateral section 94, preferably with hinge 63, forming a distal vertical section 61, operative to press against lingual cortical plate 14B.

The method of installing implant member 16, using template 90 is similar to that of using template 60 described hereinabove, in conjunction with (FIGS. 6A–6C) but includes a step of adjusting template 90 to the width of the jawbone using sliding mechanism 92.

Figure 9A:
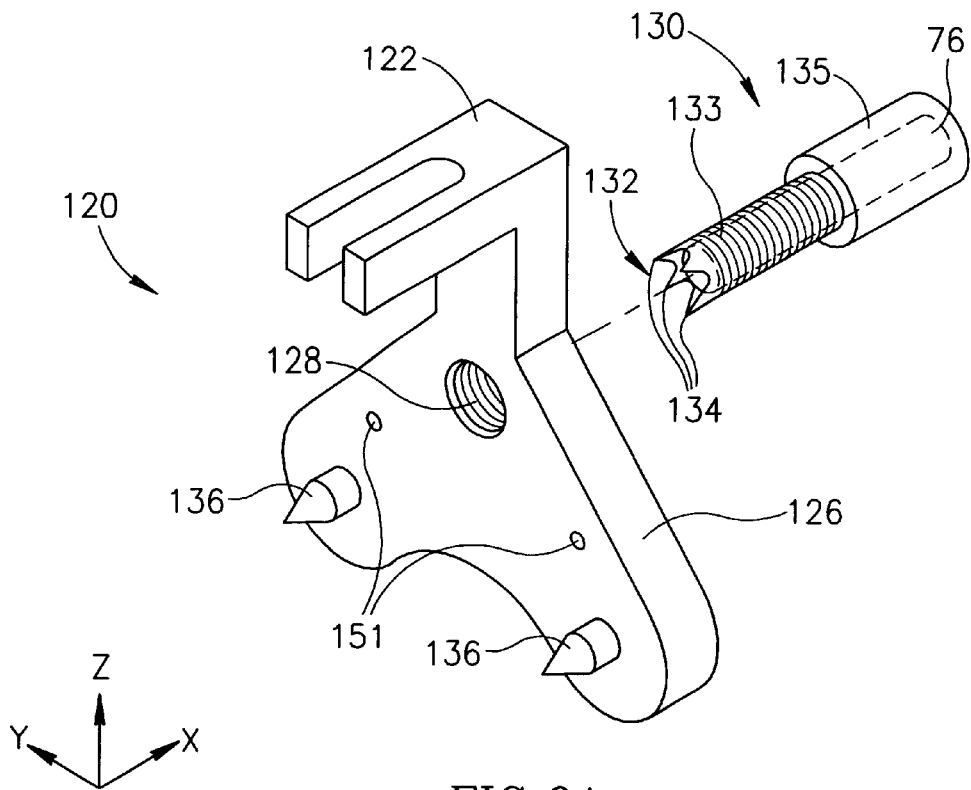
FIGS. 9A–9C together schematically illustrate a template arranged for clamping the jawbone in accordance with still another template embodiment of the present invention.
Figure 9B:
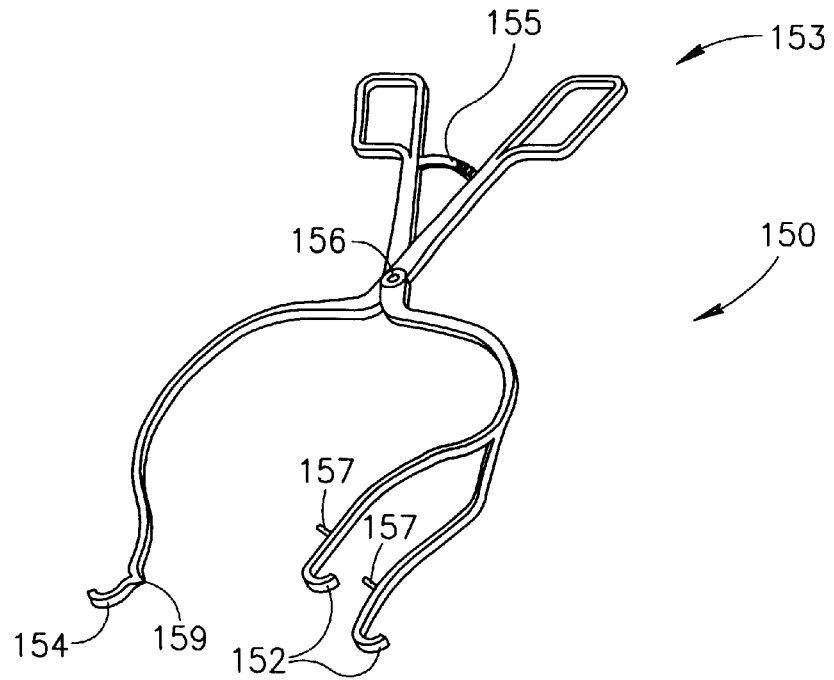
Figure 9C:
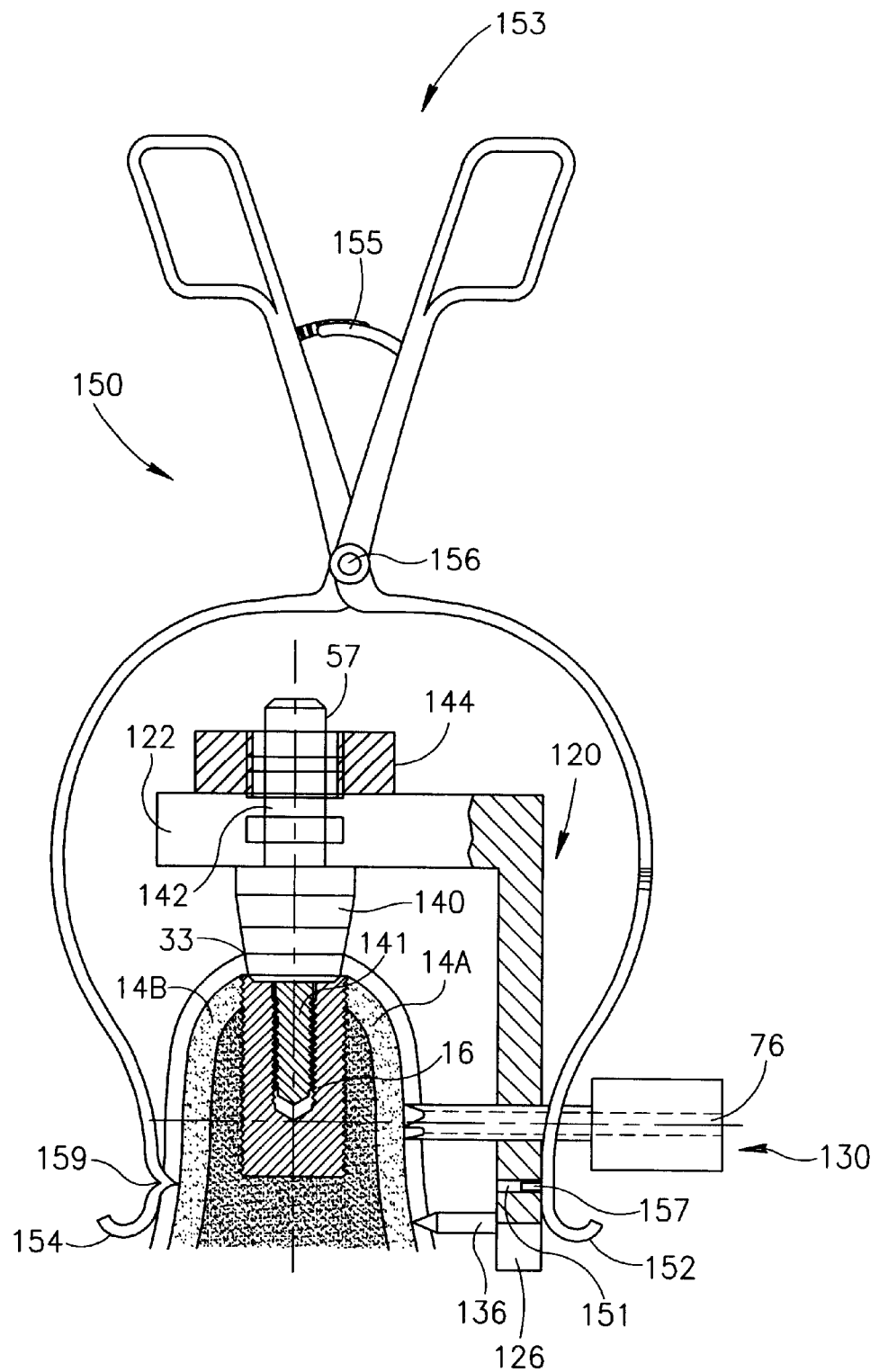

Reference is now made to FIGS. 9A–9C, which together, schematically illustrate a template 120, arranged for clamping the jawbone, while adjusting to jawbones of different widths, in accordance with a fourth template embodiment of the present invention, which is the preferred template embodiment. While most templates, and specifically, templates found in the prior art, may generally be used for the anterior segment of the mouth, template 120 may be used both for both the anterior and posterior segments of the mouth.

As seen in FIG. 9A, template 120 includes a preferably U-shaped lateral section 122, arranged to mesh with a portion of implant member 16, which protrudes from the jawbone, for example, arranged to mesh with mount 140 (FIG. 1B). Additionally, template 120 includes a proximal vertical section 126, for running generally along buccal cortical plate 14A. Proximal vertical section 126 has a through, preferably threaded, channel 128.

Template 120 further includes a hollow bolt attachment 130, which includes a threaded portion 133, complementing threaded channel 128, and a finger-gripping portion 135. Bolt attachment 130 is operative to selectably be threaded into and out of threaded channel 128, so as to selectably press against buccal cortical plate 14A and form a hold on the jawbone, and to selectably release the hold on the jawbone. Preferably, bolt attachment 130 has at a distal end 132, spikes 134. Spikes 134 are operative to pierce into buccal cortical plate 14A, when bolt attachment 130 presses against it, thus increasing the hold on the jawbone.

Hollow bolt attachment 130 forms a housing for drill-bit guide channel 76, and is operative to guide drill bit 72 (FIG. 6A), for drilling bone channel 42, while protecting the cheek from the drill bit.

In accordance with the preferred embodiment of the present invention, after it is used for guiding a drill bit into bone channel 42, and while still pressing against buccal cortical plate 14A, bolt attachment 130 may be further used to guide cortical anchor apparatus 12, such as $12_{3D}$ (FIG. 3D) into the bone. The use of bolt attachment 130, pressing against proximal cortical plate 14A, further increases the precision of inserting cortical anchor apparatus into the jawbone channel. When using another cortical anchor apparatus 12, such as $12_{3C}$ or $12_{3E}$, the hollow bolt attachment 130 can be replaced after drilling, with another attachment with a slightly larger inner hole diameter, suited to the larger proximal portion 43 of anchor apparatus $12_{3C}$ or $12_{3E}$. Alternatively, hollow bolt 130 may contain an inner hollow tube that can be removed from the bolt after the initial phase of drilling. The larger diameter thus produced can provide for the larger diameter required by proximal portion 43 of anchor apparatus $12_{3C}$ or $12_{3E}$.

Furthermore, template 120 includes at least one spike 136, on proximal vertical section 126, for piercing buccal cortical plate 14A, when bolt attachment 130 presses against it, to increase the hold on the jawbone. Alternatively, two or more spikes 136 may be used. At least one spike 136 may be substantially at the same elevation, or same z value, as bolt attachment 130, or at a different elevation. Two or more spikes 136 may be at the same elevation, or same z value, with respect to each other, or at different elevations. At least one spike 136 is arranged to pierce through gingival tissue 65 (FIG. 1A) and anchor with respect to buccal cortical plate 14A.

Generally, implant member 16 is provided with a mount 140 (FIG. 1B), threaded into cervix 30 (FIG. 1B). After insertion into bore 20, mount 140 is removed. In accordance with the present embodiment of the invention, lateral section 122 is arranged to slide over a post 142 of mount 140, so as to mesh with it. A nut 144 may then be used to lock template 120 in place, on mount 140. Preferably, mount 140 includes alignment indicator 57 (FIG. 9C), to indicate the orientation of through conduit 46 (FIG. 1A).

Alternatively, superstructure 33 (FIG. 1A) or mount 140 (FIG. 1B) may be used in place of post 142, and lateral section 122 may be arranged to complement it.

As seen in FIGS. 9B and 9C, template 120 may be used with a tri-prong ratchet 150, having a finger-gripping portion 153, a distal, flexible prong 154, and two proximal, flexible prongs 152. Ratchet 150 is operative to clamp section 126 of template 120 and lingual cortical plate 14B together, to increase the hold of template 120 over the jawbone.

Preferably, distal flexible prong 154 is arranged to press against lingual cortical plate 14B. Two proximal, flexible prongs 152 are arranged to press against section 126, on the anterior and posterior sides of bolt attachment 130.

Additionally, two proximal, flexible prongs 152 have pins 157 arranged to fit into holes 151 in section 126 (FIG. 9A), to provide increased stability. Furthermore, distal flexible prong 154 includes a spike 159, operative to pierce through gingival tissue 65 (FIG. 1A) and anchor with respect to buccal cortical plate 14B.

Preferably, ratchet 150 further includes a hinge 156 and a graduated locking mechanism 155, operative to lock against jawbones of different widths.

Figure 9D:
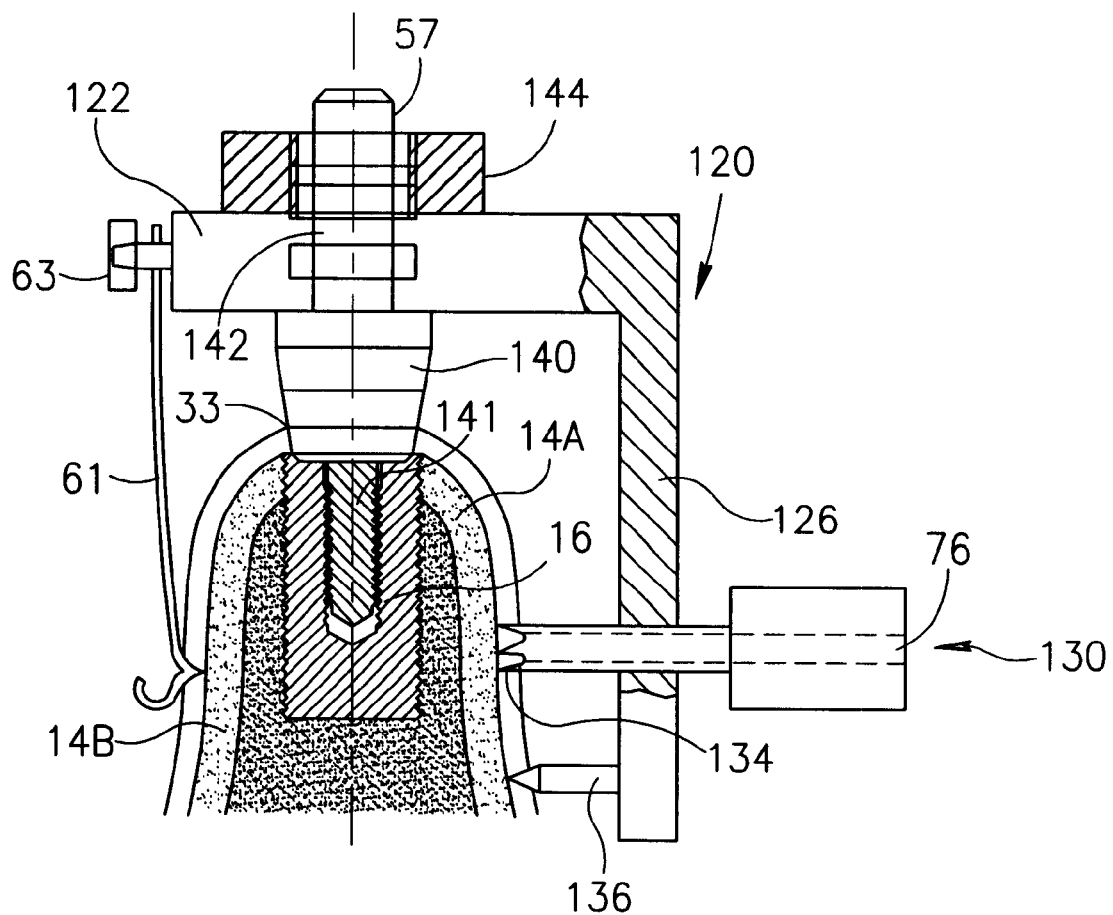
FIG. 9D schematically illustrates an alternative embodiment of templates in accordance with another template embodiment of the present invention.

Reference is now made to FIG. 9D, which schematically illustrates an alternative embodiment of template 120, wherein in place of ratchet 150, template 120 includes leaf spring 61, attached to lateral section 122, preferably with hinge 63, forming distal vertical section 61 and operative to press against lingual cortical plate 14B.

The method of installing implant member 16, using template 120 includes the following steps (see also FIG. 1A):

1. drilling a bore 20 from bone crest 28, into the jawbone, along the z-axis;
2. inserting implant member 16 into bore 20, to a predetermined depth, H, preferably, with a screwing, self-tapping motion, which cuts an internal thread in cancellous bone tissue 22;
3. meshing lateral section 122 with mount 140 (FIG. 1B) or with superstructure 33, thus aligning threaded channel 128 and hollow bolt attachment 130 with through conduit 46 of implant member 16;
4. clamping proximal vertical section 126 and lingual cortical plate 14B with ratchet 150 (FIG. 9B), or with leaf spring 61 (FIG. 9D);
5. pressing hollow bolt attachment 130 against buccal cortical plate 14A, thus preferably piercing buccal cortical plate 14A with spikes 134 and (or) 136.
6. positioning a drill bit in drill-bit guide channel 76 of hollow bolt attachment 130; and
7. drilling channel 42 (FIG. 2B) into the jawbone;

The method of the present embodiment proceeds as steps 8–11, or as steps 8A–12A of the method described hereinabove, in conjunction with FIGS. 6A–6C.

Figure 10:
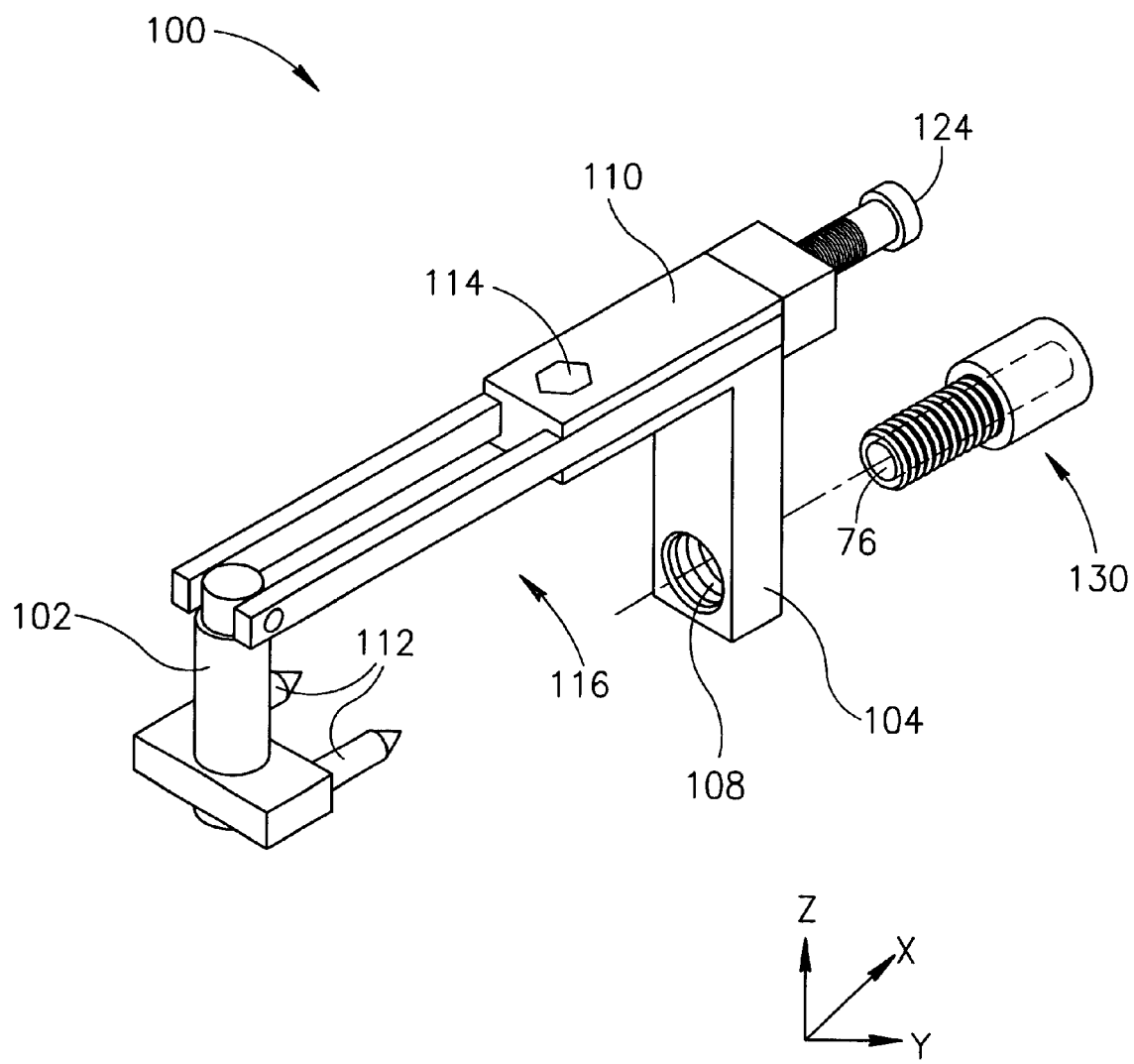
FIG. 10 schematically illustrates a template, arranged for clamping the jawbone, in accordance with yet another embodiment of the present invention.

Reference is now made to FIG. 10, which schematically illustrates a template 100, arranged for clamping the jawbone, in accordance with a fifth template embodiment of the present invention.

Template 100 includes a lateral section 110, having an aligning component 114, preferably formed as a cutout section 114 or a "carved out" section 114, arranged to mesh with a portion of implant member 16, which protrudes from the jawbone, such as superstructure 33 (FIG. 1A) or mount 140 (FIG. 1B).

Additionally, lateral section 110 includes a slide mechanism 116, controlled by a bolt 124, for adjusting to jawbones of different widths.

Furthermore, template 110 includes a distal vertical section 102, for running generally along lingual cortical plate 14B, having spikes 112, arranged to pierce lingual cortical plate 14B (FIG. 1A).

Furthermore, template 100 includes a proximal vertical section 104, for running generally along buccal cortical plate 14A. Proximal vertical section 104 includes hollow bolt attachment 130, arranged in a threaded channel 108, operative to selectably press against buccal cortical plate 14A, thus clamping the jawbone, between distal and proximal vertical sections 102 and 104.

Hollow bolt attachment 130 forms a housing for drill-bit guide channel 76, and is operative to guide drill bit 72 (FIG. 6A).

In alternative embodiments of template 100, bolt attachment 130 may include spikes 134 (FIG. 9A) and proximal vertical section 104 may include spikes 136.

The method of installing implant member 16, using template 100 is similar to that described hereinabove, in conjunction with FIGS. 9A–9D, however, preferably, after meshing lateral section 110 with a portion of implant member 16 that protrudes from the jawbone, distal vertical section 102 is positioned against lingual cortical plate 14B, and only then, proximal vertical section 104 is positioned against buccal cortical plate 14A.

A specific advantage of the present invention is that loads, generated by masticatory forces, are transferred to virgin tissue of the hard, cortical bone, thus providing primary stabilization of the tooth replacement, before bone growth occurs.

The implant members, mini-plates, screws, and the cortical anchor apparatus are preferably formed of a biocompatible material, for example, a titanium alloy, pure titanium, pure gold, ceramics, plastic or other known biocompatible metals, alloys or other materials, for tooth replacements.

A coating of bone-growth enhancing material may be applied to implant member 16.

In accordance with the present invention, reference to the lingual cortical plate is used by way of example only. Except for the discussion of FIG. 5A, which relates to a maxillary tooth replacement, references to the lingual cortical plate apply to the palatal cortical plate as well.

Although generally, the proximal cortical plate is the buccal cortical plate, in accordance with the present invention, either the buccal or the lingual cortical plates may be the proximal plate, with respect to the operator. Reference to the buccal cortical plate as the proximal cortical plate was made by way of example only.

It will be appreciated by persons skilled in the art, that the scope of the present invention is not limited by what has been specifically seen and described hereinabove, merely by way of example. Rather, the scope of the invention is limited solely by the claims, which follow.

What is claimed is:

1. A complementary system, which includes:
    an implant member, having:
        a portion which protrudes from the jawbone, when said implant member is installed in the jawbone; and
        a through conduit at a far portion with respect to an operator, invisible to the operator, when said implant member is installed in the jawbone; and
    a template, having:
        a distal vertical section, running generally along a distal cortical plate of the jawbone, operative to press against the distal cortical plate;
        a proximal vertical section, running generally along a proximal cortical plate of the jawbone, which includes:
            a drill-bit-channel housing; and
            a drill-bit guide channel, located within said drill-bit-channel housing; and
        a lateral section, arranged to mesh with said portion of said implant member which protrudes from the jawbone, thus aligning said drill-bit guide channel with said through conduit of said implant member.

2. A complementary system, according to claim 1, wherein said drill-bit guide channel is further operative to guide bi-cortical anchor apparatus for insertion into the jawbone.

3. A complementary system, according to claim 1, wherein said portion which protrudes from the jawbone is a mount that is provided with the implant member.

4. A complementary system, according to claim 1, wherein said portion, which protrudes from the jawbone, is a superstructure of the implant member.

5. A complementary system, according to claim 1 and further including a slide mechanism for adjusting to jawbones of different widths.

6. A complementary system, according to claim 1 and further including at least one spike arranged for piercing a cortical plate selected from a group which consists of said distal cortical plate and said proximal cortical plate, for increasing the hold on the jawbone.

7. A complementary system according to claim 6, wherein said at least one spike includes a plurality of spikes.

8. A complementary system, according to claim 1, wherein said at least one spike includes a plurality of spikes.

9. A complementary system, according to claim 1, wherein said drill-bit-channel housing is formed as a hollow bolt, arranged to selectably press against said proximal cortical plate.

10. A complementary system, according to claim 9 wherein said drill-bit guide channel, located within said hollow bolt, is further operative to guide bi-cortical anchor apparatus for insertion into the jawbone.

11. A complementary system, according to claim 1, wherein said distal vertical section, running generally along said distal cortical plate of the jawbone, operative to press against it, is a leaf spring.

12. A complementary system, according to claim 1, and further including a ratchet, which is arranged to clamp said template and said distal cortical plate wherein said distal vertical section, running generally along said distal cortical plate of the jawbone, operative to press against it, is a distal prong of said ratchet.

13. A complementary system, according to claim 12, wherein said ratchet further includes a locking mechanism, arranged for jawbones of different widths.

14. A complementary system, according to claim 12, wherein said ratchet is a three prong ratchet, having two proximal prongs, to the left and to the right of said drill-bit guide channel housing, along said y-axis, and having a single distal prong.

15. A complementary system, according to claim 1, wherein said implant member is arranged for insertion into a jawbone along a vertical axis of a tooth, said implant member further including:
   near and far portions;
   a cervix, at said near portion, arranged to secure a dental prosthesis thereto;
   said through conduit further arranged to support a bi-cortical anchor apparatus, without locking thereto, separated from said cervix with a solid barrier, which acts as a bacteria barrier; and
   said bi-cortical anchor apparatus, arranged for insertion into a jawbone, from a proximal cortical plate towards a distal cortical plate, said bi-cortical anchor apparatus including:
      a distal portion, having a distal effective diameter and a distal surface, operable to bite into and engage with virgin tissue of the distal cortical plate, and anchor tightly, thereto;
      a mid-portion having a mid-portion effective diameter and a mid-portion surface, operable to support said implant member without locking thereto;
      a proximal portion, having a proximal effective diameter, which is somewhat larger than both said distal and mid-portion effective diameters, and having a proximal surface which is operable to bite into and engage with virgin tissue of the proximal cortical plate, and anchor tightly, thereto; and
      a tool receptor, at the proximal-most end of said proximal portion, for interacting with a tool, to facilitate the insertion of said apparatus.

16. A complementary system, according to claim 1, wherein said implant member is arranged for insertion into a jawbone, said implant member further including:
   near and far portions;
   a cervix, at said near portion, arranged to secure a dental prosthesis thereto;
   said through conduit further arranged to support bi-cortical anchor apparatus, without locking thereto, separated from said cervix with a solid barrier, which acts as a bacteria barrier; and
   said bi-cortical anchor apparatus, arranged for insertion into a jawbone, from a proximal cortical plate towards a distal cortical plate, said bi-cortical anchor apparatus including:
      a distal portion, having a distal effective diameter and a distal surface, operable to bite into and engage with a tissue of the distal cortical plate, and anchor tightly, thereto;
      a mid-portion, having a mid-portion effective diameter and a mid-portion surface, operable to support an implant member without locking thereto;
      a proximal portion, having a proximal effective diameter and a proximal surface which is operable to bite into and engage with a tissue of the proximal cortical plate, and anchor tightly, thereto; and
      a tool receptor, at the proximal-most end of said proximal portion, for interacting with a tool, to facilitate the insertion of said apparatus.

17. Bi-cortical anchor apparatus, arranged for insertion into a jawbone, from a proximal cortical plate towards a distal cortical plate, said bi-cortical anchor apparatus including:
   a distal portion, having a distal effective diameter and a distal surface, operable to bite into and engage with virgin tissue of the distal cortical plate, and anchor tightly, thereto;
   a mid portion, having a mid-portion effective diameter and a mid-portion surface, operable to support an implant member without locking thereto;
   a proximal portion, having a proximal effective diameter, which is somewhat larger than both said distal and mid-portion effective diameters, and having a proximal surface which is operable to bite into and engage with virgin tissue of the proximal cortical plate, and anchor tightly, thereto; and
   a tool receptor, at the proximal-most end of said proximal portion, for interacting with a tool, to facilitate the insertion of said apparatus, said tool receptor being a threaded internal cervix, arranged to interact with a tool, said tool having:
      proximal and distal portions with respect to the operator;
      a threaded surface, at said distal portion, which complements said threaded internal cervix;
      a finger-gripping portion at said proximal portion; and
      a stem, connecting said proximal and distal portions, and
      wherein said tool is operable to guide said apparatus through a template drill-bit guide channel.

18. Bi-cortical anchor apparatus, arranged for insertion into a jawbone, from a proximal cortical plate towards a distal cortical plate, said bi-cortical anchor apparatus including:
   a distal portion, having a distal effective diameter and a distal surface, operable to bite into and engage with a tissue of the distal cortical plate, and anchor tightly, thereto;
   a mid portion, having a mid-portion effective diameter and a mid-portion surface, operable to support an implant member without locking thereto;
   a proximal portion, having a proximal effective diameter and a proximal surface which is operable to bite into and engage with a tissue of the proximal cortical plate, and anchor tightly, thereto; and a tool receptor, at the proximal-most end of said proximal portion, for interacting with a tool, to facilitate the insertion of said apparatus, and wherein said proximal and distal effective diameters are substantially the same, and wherein said mid-portion effective diameter is somewhat smaller.

19. Bi-cortical anchor apparatus, arranged for insertion into a jawbone, from a proximal cortical plate towards a distal cortical plate, said bi-cortical anchor apparatus including:

a distal portion, having a distal effective diameter and a distal surface, operable to bite into and engage with a tissue of the distal cortical plate, and anchor tightly, thereto;

a mid portion, having a mid-portion effective diameter and a mid-portion surface, operable to support an implant member without locking thereto;

a proximal portion, having a proximal effective diameter and a proximal surface which is operable to bite into and engage with a tissue of the proximal cortical plate, and anchor tightly, thereto; and a tool receptor, at the proximal-most end of said proximal portion, for interacting with a tool, to facilitate the insertion of said apparatus, wherein said tool receptor is a threaded internal cervix, arranged to interact with a tool, having:

proximal and distal portions with respect to the operator;

a threaded surface, at said distal portion, which complements said threaded internal cervix;

a finger-gripping portion at said proximal portion; and a stem, connecting said proximal and distal portions, wherein said tool is operable to guide said apparatus through a template drill-bit guide channel.

20. A method of installing an implant member which includes:

drilling a bore from bone crest into the jawbone;

inserting an implant member, having a through conduit, into the bore;

positioning a template, while meshing a lateral section of the template with a portion of the implant member which protrudes from the jaw, thus aligning a drill-bit guide channel with the through conduit of the implant member;

clamping said jawbone between a proximal vertical section and a distal vertical section of the template and between the proximal vertical section of the template and at least one distal leaf spring;

drilling a channel in the jawbone, through the drill-bit guide channel of the template;

inserting bi-cortical anchor apparatus from the proximal cortical plate, through the bone channel and then through conduit of the implant member, towards the distal cortical plate, for bi-cortical retention, while self-tapping an internal thread into the bone channel;

anchoring the distal portion of the bi-cortical anchor apparatus, by biting into tissue of the distal cortical plate and engaging thereto; and anchoring the proximal portion of the bi-cortical anchor apparatus by biting into tissue of the proximal cortical plate and engaging thereto.

21. A method of installing an implant member which includes:

drilling a bore from bone crest into the jawbone;

inserting an implant member, having a through conduit, into the bore;

positioning a template, while meshing a lateral section of the template with a portion of the implant member which protrudes from the jaw, thus aligning a drill-bit guide channel with the through conduit of the implant member;

clamping said jawbone between a proximal vertical section and a distal vertical section of the template with a ratchet;

drilling a channel in the jawbone, through the drill-bit guide channel of the template;

inserting bi-cortical anchor apparatus from the proximal cortical plate, through the bone channel and then through conduit of the implant member, towards the distal cortical plate, for bi-cortical retention, while self-tapping an internal thread into the bone channel;

anchoring the distal portion of the bi-cortical anchor apparatus, by biting into tissue of the distal cortical plate and engaging thereto; and anchoring the proximal portion of the bi-cortical anchor apparatus by biting into tissue of the proximal cortical plate and engaging thereto.

22. A method of installing an implant member which includes:

drilling a bore from bone crest into the jawbone;

inserting an implant member, having a through conduit, into the bore, positioning a template, while meshing a lateral section of the template with a portion of the implant member which protrudes from the jaw, thus aligning a drill-bit guide channel with the through conduit of the implant member;

clamping said jawbone between a proximal vertical section and a distal vertical section of the template and piercing at least one cortical plate with spikes;

drilling a channel in the jawbone, through the drill-bit guide channel of the template;

inserting bi-cortical anchor apparatus from the proximal cortical plate, through the bone channel and then through conduit of the implant member, towards the distal cortical plate, for bi-cortical retention, while self-tapping an internal thread into the bone channel;

anchoring the distal portion of the bi-cortical anchor apparatus, by biting into tissue of the distal cortical plate and engaging thereto; and anchoring the proximal portion of the bi-cortical anchor apparatus by biting into tissue of the proximal cortical plate and engaging thereto.

23. A method of installing an implant member which includes:

drilling a bore from bone crest into the jawbone and into the sinus cavity;

inserting an implant member, having a through conduit, into the bore;

positioning a template, while meshing a lateral section of the template with a portion of the implant member which protrudes from the jaw, thus aligning a drill-bit guide channel with the through conduit of the implant member;

drilling a channel in the jawbone, through the drill-bit guide channel of the template;

inserting bi-cortical anchor apparatus from the proximal cortical plate, through the bone channel and then through conduit of the implant member, towards the distal cortical plate, for bi-cortical retention, while self-tapping an internal thread into the bone channel;

anchoring the distal portion of the bi-cortical anchor apparatus, by biting into tissue of the distal cortical plate and engaging thereto; and anchoring the proximal portion of the bi-cortical anchor apparatus by biting into tissue of the proximal cortical plate and engaging thereto.

24. A complementary system, which includes:

an implant member, having:
- a portion which protrudes from the jawbone, when said implant member is installed in the jawbone; and
- a through conduit at a far portion with respect to an operator, invisible to the operator, when said implant member is installed in the jawbone; and a template, having:
- a distal vertical section, running generally along a distal cortical plate of the jawbone, operative to press against the distal cortical plate, and wherein said distal vertical section is a leaf spring;
- a proximal vertical section, running generally along a proximal cortical plate of the jawbone, which includes:
  - a drill-bit-channel housing;
  - a drill-bit guide channel, located within said drill-bit-channel housing; and
  - a lateral section, arranged to mesh with said portion of said implant member which protrudes from the jawbone, thus aligning said drill-bit guide channel with said through conduit of said implant member.

25. A complementary system, which includes:

an implant member, having:
- a portion which protrudes from the jawbone, when said implant member is installed in the jawbone; and
- a through conduit at a far portion with respect to an operator, invisible to the operator, when said implant member is installed in the jawbone; and a template, having:
- a distal vertical section, running generally along a distal cortical plate of the jawbone, operative to press against the distal cortical plate;
- a proximal vertical section, running generally along a proximal cortical plate of the jawbone, which includes:
  - a drill-bit-channel housing; and
  - a drill-bit guide channel, located within said drill-bit-channel housing;
  - a lateral section, arranged to mesh with said portion of said implant member which protrudes from the jawbone, thus aligning said drill-bit guide channel with said through conduit of said implant member; and
  - a ratchet, which is arranged to clamp said template and said distal cortical plate wherein said distal vertical section, running generally along said distal cortical plate of the jawbone, operative to press against it, is a distal prong of said ratchet.

26. A complementary system according to claim 25, wherein said ratchet further includes a locking mechanism, arranged for jawbones of different widths.

27. A complementary system according to claim 25, wherein said ratchet is a three prong ratchet, having two proximal prongs, to the left and to the right of said drill-bit guide channel housing, along said y-axis, and having a single distal prong.

28. A complementary system, which includes:

an implant member, having:
- a portion which protrudes from the jawbone, when said implant member is installed in the jawbone; and
- a through conduit at a far portion with respect to an operator, invisible to the operator, when said implant member is installed in the jawbone; and a template, having:
- a distal vertical section, running generally along a distal cortical plate of the jawbone, operative to press against the distal cortical plate;
- a proximal vertical section, running generally along a proximal cortical plate of the jawbone, which includes:
  - a drill-bit-channel housing; and
  - a drill-bit guide channel, located within said drill-bit-channel housing;
- a lateral section, arranged to mesh with said portion of said implant member which protrudes from the jawbone, thus aligning said drill-bit guide channel with said through conduit of said implant member; and
- at least one spike arranged for piercing a cortical plate selected from a group which consists of said distal cortical plate and said proximal cortical plate, for increasing the hold on the jawbone.

* * * * *